United States Patent
Leschinsky

(10) Patent No.: US 8,753,283 B2
(45) Date of Patent: Jun. 17, 2014

(54) AUTOMATIC DEVICES FOR REMOTE ISCHEMIC PRECONDITIONING

(75) Inventor: Boris Leschinsky, Mahwah, NJ (US)

(73) Assignee: Infarct Reduction Technologies Inc., Waldwick, NJ (US)

( * ) Notice: Subject to any disclaimer, the term of this patent is extended or adjusted under 35 U.S.C. 154(b) by 60 days.

(21) Appl. No.: 13/362,039

(22) Filed: Jan. 31, 2012

(65) Prior Publication Data
US 2012/0130419 A1     May 24, 2012

Related U.S. Application Data

(63) Continuation of application No. 12/820,273, filed on Jun. 22, 2010, now Pat. No. 8,114,026.

(60) Provisional application No. 61/219,536, filed on Jun. 23, 2009, provisional application No. 61/256,038, filed on Oct. 29, 2009.

(51) Int. Cl.
*A61B 5/02* (2006.01)
*A61B 17/00* (2006.01)

(52) U.S. Cl.
USPC ............ 600/490; 606/201; 606/202; 600/481

(58) Field of Classification Search
USPC .......................... 600/481, 483, 485, 490–504; 606/201–203
See application file for complete search history.

(56) References Cited

U.S. PATENT DOCUMENTS

| | | | | |
|---|---|---|---|---|
| 4,664,651 A | * | 5/1987 | Weinshenker et al. | 604/115 |
| 4,690,151 A | * | 9/1987 | Utsunomiya et al. | 600/495 |
| 5,072,736 A | * | 12/1991 | Ogawa et al. | 600/493 |
| 5,267,565 A | * | 12/1993 | Beard | 600/454 |
| 5,687,732 A | * | 11/1997 | Inagaki et al. | 600/485 |
| 5,733,304 A | * | 3/1998 | Spence | 606/203 |
| 5,842,996 A | * | 12/1998 | Gruenfeld et al. | 600/490 |
| 6,152,880 A | * | 11/2000 | Okada | 600/490 |

(Continued)

FOREIGN PATENT DOCUMENTS

| | | |
|---|---|---|
| GB | 2434536 | 1/2007 |
| WO | WO/02/085199 | 10/2002 |

(Continued)

OTHER PUBLICATIONS

Takarada et al, Application of vascular occlusion diminish disuse atrophy of knee extensor muscles, Medicine & Science in Sports & Exercise, vol. 32, No. 12 2000, pp. 2035-2039.*

(Continued)

*Primary Examiner* — Navin Natnithithadha
(74) *Attorney, Agent, or Firm* — Boris Leschinsky

(57) ABSTRACT

Single- or dual-bladder devices for remote ischemic preconditioning and blood pressure monitoring are disclosed along with various oscillometry-based and other methods for detecting systolic and diastolic blood pressure while the ischemic preconditioning treatment is in progress. The devices and methods of the invention provide for delivery of ischemic preconditioning at the lowest effective cuff pressure while closely monitoring patient's hemodynamics. Advantageously, the device of the invention allows both ischemic preconditioning and blood pressure monitoring to be done on the same limb. Disposable battery-powered version of the device of the present invention is especially useful for emergency use with patients suffering from acute myocardial infarction, acute stroke, or acute trauma. Additional device configurations are described for use in a percutaneous intervention and vascular sealing settings.

4 Claims, 7 Drawing Sheets

(56) References Cited

U.S. PATENT DOCUMENTS

| | | | | |
|---|---|---|---|---|
| 6,152,881 | A * | 11/2000 | Raines et al. | 600/507 |
| 6,251,080 | B1 * | 6/2001 | Henkin et al. | 600/490 |
| 6,344,025 | B1 * | 2/2002 | Inagaki et al. | 600/490 |
| 6,361,548 | B1 * | 3/2002 | McEwen | 606/201 |
| 6,478,745 | B2 * | 11/2002 | Nakagawa et al. | 600/499 |
| 6,682,547 | B2 * | 1/2004 | McEwen et al. | 606/202 |
| 6,858,012 | B2 * | 2/2005 | Burns et al. | 600/483 |
| 6,962,599 | B2 * | 11/2005 | Hui | 606/202 |
| 7,048,702 | B2 * | 5/2006 | Hui | 601/152 |
| 7,314,478 | B2 * | 1/2008 | Hui | 606/202 |
| 7,331,977 | B2 * | 2/2008 | McEwen et al. | 606/202 |
| 7,338,410 | B2 | 3/2008 | Dardik | |
| 7,374,540 | B2 * | 5/2008 | Schnall | 600/481 |
| 7,384,425 | B2 * | 6/2008 | McEwen | 606/201 |
| 7,390,303 | B2 * | 6/2008 | Dafni | 600/500 |
| 7,717,855 | B2 | 5/2010 | Caldarone et al. | |
| 7,758,607 | B2 * | 7/2010 | McEwen et al. | 606/203 |
| 7,771,453 | B2 * | 8/2010 | McEwen et al. | 606/203 |
| 7,780,698 | B2 * | 8/2010 | McEwen et al. | 606/203 |
| 7,885,710 | B2 | 2/2011 | Sih | |
| 7,909,849 | B2 * | 3/2011 | McEwen | 606/201 |
| 8,114,026 | B2 * | 2/2012 | Leschinsky | 600/490 |
| 8,123,694 | B2 * | 2/2012 | Kinsley et al. | 600/492 |
| 8,137,378 | B2 * | 3/2012 | McEwen et al. | 606/203 |
| 8,246,548 | B2 | 8/2012 | Naghavi | |
| 2001/0029389 | A1 * | 10/2001 | Kim | 606/203 |
| 2002/0147404 | A1 * | 10/2002 | Kato et al. | 600/503 |
| 2003/0065270 | A1 * | 4/2003 | Raines et al. | 600/504 |
| 2005/0177078 | A1 * | 8/2005 | Loeb et al. | 601/152 |
| 2007/0005106 | A1 * | 1/2007 | Adducci | 606/202 |
| 2007/0150005 | A1 | 6/2007 | Sih et al. | |
| 2007/0160645 | A1 | 7/2007 | Vinten-Johansen | |
| 2008/0081963 | A1 * | 4/2008 | Naghavi et al. | 600/301 |
| 2008/0139949 | A1 | 6/2008 | Caldarone et al. | |
| 2009/0137884 | A1 | 5/2009 | Naghavi et al. | |
| 2009/0287069 | A1 | 11/2009 | Naghavi et al. | |
| 2009/0318818 | A1 * | 12/2009 | Whitaker et al. | 600/495 |
| 2010/0105993 | A1 | 4/2010 | Naghavi | |
| 2010/0160799 | A1 | 6/2010 | Caldarone | |
| 2010/0185220 | A1 | 7/2010 | Naghavi | |
| 2010/0292619 | A1 | 11/2010 | Redington | |
| 2010/0305607 | A1 | 12/2010 | Caldarone | |
| 2010/0324429 | A1 | 12/2010 | Leschinsky | |
| 2011/0077701 | A1 | 3/2011 | Sih et al. | |
| 2011/0190807 | A1 | 8/2011 | Redington | |
| 2011/0208099 | A1 | 8/2011 | Naghavi | |
| 2011/0224606 | A1 | 9/2011 | Shome | |
| 2011/0238107 | A1 | 9/2011 | Raheman | |
| 2011/0240043 | A1 | 10/2011 | Redington | |
| 2011/0251635 | A1 | 10/2011 | Caldarone | |
| 2011/0319732 | A1 | 12/2011 | Naghavi et al. | |
| 2012/0130419 | A1 * | 5/2012 | Leschinsky | 606/202 |
| 2012/0277789 | A1 | 11/2012 | Caldarone | |

FOREIGN PATENT DOCUMENTS

| | | |
|---|---|---|
| WO | WO/2008/070164 | 6/2008 |
| WO | WO/2008/148045 | 12/2008 |
| WO | WO/2008/148062 | 12/2008 |
| WO | WO/2011/005538 | 1/2011 |
| WO | WO/2011/121402 | 10/2011 |
| WO | WO/2012/016280 | 2/2012 |
| WO | WO/2012/090068 | 7/2012 |
| WO | WO/2012/142360 | 10/2012 |

OTHER PUBLICATIONS

Moore et al, Neuromuscular adaptations in human muscle following low intensity resistance training with vascular occlusion, Eur J Appl Physiol (2004) 92: 399-406.*

Günaydin B, Cakici I, Soncul H et al. Does remote organ ischaemia trigger cardiac preconditioning during coronary artery surgery? Pharmacological Research 41;4:493-496, 2000.

Loukogeorgakis SP et al. Remote ischemic preconditioning provides early and late protection against endothelial ischemia-reperfusion injury in humans. JACC 46;3:450-456, 2005.

Cheung MMH et al. Randomized controlled trial of the effects of remote ischemic preconditioning on children undergoing cardiac surgery. JACC 47;11:2277-2282, 2006.

Ali ZA et al. Remote ischemic preconditioning reduces myocardial and renal injury after elective abdominal aortic aneurysm repair: a randomized controlled trial. Circulation 116:198-1105, 2007.

Hoole SP et al. Cardiac remote ischemic preconditioning in coronary stenting (CRISP Stent) study: a prospective, randomized control trial. Circulation 119:820-827, 2009.

Rentoukas I et al. Cardioprotective effect of remote ischemic periconditioning in primary percutaneous coronary intervention; enhancement by opioid action. J Am Coll Cardiol Intv 3:49-55, 2010.

Botker HE et al. Remote ischaemic conditioning before hospital admission, as a complement to angioplasty, and effect on myocardial salvage in patients with acute myocardial infarction: a randomized trial. Lancet 375:727-34, 2010.

Thielmann M, Kottenberg E, Boengler K, Raffelsieper C, Neuhaeuser M, Peters J, Jakob H and Heusch G. Remote ischemic preconditioning reduces myocardial injury after coronary artery bypass surgery with crystalloid cardioplegic arrest. Basic Res Cardiol 105(5):657-64, 2010.

Walsh SR, Tang T, Sadat U, Dutka DP, Gaunt ME. Cardioprotection by remote ischaemic preconditioning. Br J Anaesthesia 99;5:611-616, 2007.

Hausenloy DJ, Yellon DM. Remote ischaemic preconditioning: underlying mechanisms and clinical application. Cardiovasc Res 79:377-386, 2008.

Tapuria N, Kumar Y, Habib MM, Amara MA, Seifalian AM, Davidson BR. Remote ischemic preconditioning: a novel protective method from ischemia reperfusion injury—a review. J Surg Res 150;2:304-330, 2008.

Walsh SR, Tang TY, Sadat U, Gaunt ME. Remote ischemic preconditioning in major vascular surgery. J Vasc Surg 49:240-243, 2009.

Kharbanda RK, Nielsen TT, Redington AN. Translation of remote ischemic preconditioning into clinical practice. Lancet 374:1557-1565, 2009.

Rohilla A, Rohilla S, Singh G, Singh R. Myocardial ischemic preconditioning: a novel approach to cardioprotection. J Pharm Res 3;1:132-140, 2010.

Kharbanda RK, Mortensen, White PA et al. Transient limb ischemia induces remote ischemic preconditioning in-vivo. Circulation 106:2881-2883, 2002.

* cited by examiner

AUTOMATIC DEVICES FOR REMOTE ISCHEMIC PRECONDITIONING

CROSS-REFERENCE DATA

This application is a continuation of my U.S. patent application Ser. No. 12/820,273 entitled "METHODS AND DEVICES FOR REMOTE ISCHEMIC PRECONDITIONING AND NEAR-CONTINUOUS BLOOD PRESSURE MONITORING" filed Jun. 22, 2010, now U.S. Pat. No. 8,114,026 which in turn claims a priority benefit from the U.S. Provisional Patent Application No. 61/219,536 filed Jun. 23, 2009 entitled "BLOOD PRESSURE CUFF INCORPORATING A PRECONDITIONING DEVICE" and the U.S. Provisional Patent Application No. 61/256,038 filed Oct. 29, 2009 entitled "PRECONDITIONING DEVICES FOR USE IN AMI AND PERCUTANEOUS INTERVENTION SETTINGS", all three documents incorporated herein by reference in their entireties.

BACKGROUND OF THE INVENTION

The present invention relates generally to methods and devices aimed at reducing a harmful effect of ischemia and reperfusion injury of an organ with the overall purpose of reducing the final infarct size and loss of function by the organ. More particularly, the invention describes methods and designs for blood pressure cuffs configured to deliver remote ischemic preconditioning and monitor blood pressure of the patient.

Coronary heart disease is a leading cause of mortality and morbidity in the Western world and is projected to be a leading cause of death worldwide by year 2020. Acute myocardial infarction (AMI) is the main cause of such mortality. Although major advances in treatments over the last four decades have translated into a considerable decline in mortality rates after AMI, heart failure became a common complication for survivors, with the estimated post-infarct incidences between 10% and 40%. Post-infarct heart failure is a debilitating disease associated with high mortality, with a median survival of only 4 years. In the United States, the American Heart Association estimates the total number of patients living with heart failure today to be 5.3 million with 660 thousand new patients diagnosed every year. Direct and indirect treatments for these patients cost approximately $35 billion a year representing the single highest disease burden of all healthcare costs.

In patients with acute myocardial infarction, rapid restoration of blood flow (reperfusion) either by primary percutaneous coronary intervention or thrombolysis is the most effective treatment for myocardial salvage. However, it has now been shown that reperfusion itself has the potential to induce additional lethal injury that is not present at the end of the ischemic period. This injury is called an ischemia/reperfusion injury or simply a reperfusion injury. Reperfusion injury is a contributing factor in many other diseases, most notably including acute stroke, acute trauma, acute compartment syndrome, etc. Management of planned ischemia events during CABG, AAA and other types of surgery may also benefit from reducing the consequences of reperfusion injury.

A new treatment to induce ischemic tolerance and reduce the harmful effects of reperfusion injury is known as ischemic preconditioning. Other terms used in the literature to describe this intervention include "ischemic postconditioning", "ischemic perconditioning", and "ischemic conditioning". For the purposes of this description, all procedures describing a series of sub-lethal interruptions of blood flow are described using the general term "ischemic preconditioning" whether it is done prior to, during, or after the ischemia as well as prior to, during, or after reperfusion. Remote ischemic preconditioning describes one version of this treatment, which includes applying a series of brief sub-lethal episodes of ischemia and reperfusion to an organ other than the target ischemic organ (such ischemic organ may be a heart or a brain). This treatment triggers activation of Reperfusion Injury Salvage Kinases (RISK) pathways as well as strong anti-apoptosis and anti-inflammatory effects. Applying a series of brief ischemic stimulae to a distant organ before, during, or after restoration of normal perfusion of the target ischemic organ is shown to activate protection from ischemia for the whole body and therefore reduces ischemia-reperfusion damage of the target organ. Over the years, a number of distant organs have been shown to provide cardioprotection in the setting of remote ischemic preconditioning including skeletal muscles on upper and lower extremities. Applying a preconditioning procedure externally to an upper or lower limb is especially attractive as it is non-invasive, easy to implement, and safe. Blood flow to the limb during the procedure is typically occluded for 3-5 min by a manually- or automatically-inflated blood pressure cuff or a tourniquet cuff. A deflation interval of 3-5 min then follows and this cycle is repeated 3-4 times. An overview of this procedure and the mechanisms of action are described for example by Kharbanda R K, Nielsen T T, and Redington A N. "Translation of remote ischemic preconditioning into clinical practice", *Lancet* 374:1557-1565, 2009, incorporated herein by reference in its entirety.

Although the following description discusses applying remote ischemic preconditioning to a subject or patient (both terms are used to mean the same for the purposes of this specification) suffering from acute myocardial infarction to reduce infarct size, it is not limited to this clinical application alone. As mentioned above, this treatment can be applied to acute stroke and trauma patients including those suffering from traumatic brain injury, as well as to patients during, prior or after various interventions or surgeries when blood flow to an organ is temporarily interrupted or a release of embolic particles is likely. They can also be applied in organ and tissue transplant surgeries as well as in other clinical applications.

U.S. Pat. No. 7,717,855 to Caldarone et al. incorporated herein by reference in its entirety discloses one example of an automatic device configured to deliver remote ischemic preconditioning by periodic inflation and deflation of a cuff placed about a limb of a patient. Blood flow through the limb is interrupted by inflating the cuff to a set pressure above the systolic blood pressure of the patient. One sited example of such set pressure is 200 mmHg. This approach has a limitation in that inflating the cuff to such high pressure for extended periods of time may cause pain and discomfort to the patient. For most of the patients, there is no need to inflate the cuff to 200 mmHg to achieve total limb occlusion. On the other hand, in a small portion of the patients with high or rapidly changing blood pressure (with systolic blood pressure exceeding 200 mmHg), the set inflation pressure approach may not be sufficient to occlude the limb adequately.

Patients suffering from an acute myocardial infarction or stroke require close monitoring of their vital signs and blood pressure in particular. Deterioration of blood pressure may cause profound ischemia and multi-organ failure. Emergency medicine guidelines recommend checking patient's blood pressure every 3-5 minutes especially after administering vasodilators such as nitroglycerin. It is envisioned that upon a first contact with a medical practitioner and confirmation of diagnosis, a heart attack patient would need initiation of ischemic preconditioning and vital signs monitoring almost at the same time. Occupying one arm with a preconditioning cuff will require using another arm for a traditional blood pressure monitoring cuff. This two-arm arrangement is not only cumbersome but may also cause interruption of intra-venous injections during the periods of blood pressure measurements when the cuff is inflated and occludes blood flow to the arm.

It is therefore desirable to frequently monitor blood pressure for signs of hemodynamic deterioration and conduct ischemic preconditioning on the same arm, leaving the second arm for uninterrupted intra-venous injections. The need also exists for a device capable of delivering preconditioning at the lowest possible cuff pressure so as to reduce patient's discomfort and pain.

SUMMARY OF THE INVENTION

According to one aspect of the invention, devices and methods for remote ischemic preconditioning treatment are provided. The treatment protocol includes at least one or preferably 3 to 5 treatment cycles; each cycle includes intervals of cuff inflation, an ischemic duration lasting for at least about a minute, cuff deflation, and reperfusion duration. The cuff of the device is maintained at a minimum inflation pressure, which may be at or below the systolic blood pressure of the subject. To assure at least a substantial reduction or preferably a total cessation of blood flow through the limb during the ischemic duration, the cuff inflation pressure may be maintained at a level at or above the limb occlusion pressure. The width of the cuff is selected to be sufficiently wide so as to define the limb occlusion pressure to be below the systolic blood pressure of the subject.

Maintaining the cuff in a minimum limb occlusion state (defined by keeping the cuff pressure at or above the limb occlusion pressure and below the systolic blood pressure) during at least a portion of the ischemic duration interval allows to minimize subject's pain and discomfort while at the same time providing a unique opportunity to monitor subject's systolic blood pressure without allowing for reperfusion of the limb.

In another aspect of the invention, the remote ischemic preconditioning device is provided to include a cuff and a controller configured to inflate and deflate the cuff according to a preconditioning treatment protocol, the controller is further configured for hemodynamic surveillance during and in parallel with the preconditioning treatment protocol. The hemodynamic surveillance includes at least once detecting systolic blood pressure during an ischemic duration interval when the cuff pressure is maintained between the limb occlusion pressure and the systolic blood pressure of the subject. The hemodynamic surveillance may further include at least once detecting diastolic blood pressure during the limb reperfusion duration interval. In another aspect of the invention, systolic and diastolic blood pressures are determined periodically, on a frequent or a near-continuous basis.

Various methods may be employed to detect systolic blood pressure while the cuff is at a minimum limb occlusion state. For example, Korotkoff sounds may be detected by various sensors incorporated into the cuff such as a microphone. Another method is to measure a portion of the oscillometric envelope curve in the vicinity of the systolic pressure. If a deviation of the curve from that which is previously measured is detected, a new systolic blood pressure value may be determined by matching the pulsations amplitude to that corresponding to a previously detected value of systolic pressure. The pressure range defining the minimum limb occlusion state is then adjusted. Other methods may also be used to determine the current value of systolic blood pressure from the oscillometric envelope such as for example a derivative oscillometry where the systolic pressure is defined by a maximum of the first derivative of the oscillometric envelope curve. The portion of that curve may be continuously of periodically updated by dithering or varying the cuff pressure about the previously detected value of systolic blood pressure—all without compromising occlusion of the limb.

According to another aspect of the invention, the cuff of the device includes more than one bladder, such as for example a first and a second bladder. In another embodiment of the invention, the first bladder is designated as a proximal bladder and the second bladder is designated as a distal bladder. For the purposes of this description, the term proximal refers to that closer to the heart while the term distal refers to that closer to the periphery of the circulatory system. In case of a limb of a subject being an upper arm for example, the proximal bladder would be that located above the distal bladder. Having more than one bladder located adjacent to one another and having the same circumference allows a great deal of flexibility in operating the cuff of the invention. For example, to detect the current value of systolic blood pressure, the proximal cuff may be used to gradually decrease the pressure applied to the limb, while the distal cuff may be used for detecting a rapid or abrupt increase in pulsations amplitude indicating that the proximal cuff pressure has reached the systolic blood pressure value. At other times, both bladders may be inflated to the same pressure, providing in essence the limb occluding function of a wider cuff.

In another aspect of the invention, a device for remote ischemic preconditioning includes a cuff configured to retract about a limb of a subject, the cuff having an inflated state to reduce blood flow through the limb and a deflated state. The device further includes a controller connected to the cuff and including a first inflation assembly configured to inflate and deflate the cuff to the inflated state and the deflated state respectively according to a preconditioning treatment protocol. The treatment protocol includes a plurality of treatment cycles, each cycle comprising: cuff inflation, an ischemic duration, cuff deflation, and reperfusion duration. The controller further including a port for attaching a second inflation assembly adapted for measuring blood pressure of the subject through the cuff. The controller is further configured to connect the port to the cuff only during the cuff deflation and reperfusion duration periods of at least one of the treatment cycles. The second inflation assembly may include a manual inflation bulb or a non-invasive blood pressure monitor.

In a further aspect of the invention, the device for remote ischemic preconditioning includes a first cuff configured to retract about a limb of a subject, the first cuff having an inflated state to reduce blood flow through said limb and a deflated state. The device further includes a controller connected to the first cuff and including a first inflation assembly configured to inflate and deflate the first cuff to the inflated state and the deflated state respectively according to a preconditioning treatment protocol including a plurality of treatment cycles, each cycle comprising the first cuff inflation, an ischemic duration, the first cuff deflation, and a reperfusion duration. The device further including a second cuff configured to measure blood pressure of the subject on the same limb as used for ischemic preconditioning treatment. The controller is further optionally configured to measure the subjects' blood pressure via the second cuff during deflation of the first cuff or reperfusion duration intervals of at least one of the treatment cycles.

In a further aspect of the invention, the controller is battery-powered and incorporated with the preconditioning cuff of the device. In yet another aspect of the invention, the device includes a countdown timer of a predetermined interval of time such as 2 hours upon a completion of the preconditioning treatment protocol. In yet another aspect of the invention, the remote ischemic preconditioning device includes a sterile cover sized to completely wrap about the cuff while on the limb of the subject.

In another aspect of the invention, the remote ischemic preconditioning device is provided, the device comprising a cuff configured to retract about an upper arm of a subject, the cuff including a bladder having an inflated state to reduce blood flow through the upper arm and a deflated state, a controller connected to the bladder and including an inflation assembly configured to inflate and deflate the bladder to the inflated state and the deflated state respectively according to a preconditioning treatment protocol. The treatment protocol includes a plurality of treatment cycles, each cycle comprising: cuff inflation, an ischemic duration, cuff deflation, and a reperfusion duration. The inflation assembly is further configured to complete the cuff inflation in 30 seconds or more. In another aspect of the invention, the inflation assembly includes an air pump with flow rate less than about 0.1 cubic feet per minute.

In a further aspect of the invention, the automatic remote ischemic preconditioning device is provided as described above, the controller containing a single START button operable to initiate the ischemic preconditioning treatment, the controller further configured to conduct and finish the entire treatment protocol without further user input.

In yet another aspect of the invention, there is provided a remote ischemic preconditioning device comprising a cuff configured to retract about a limb of a subject and including one or two bladders having an inflated state to reduce blood flow through said limb and a deflated state. The device further includes a controller connected to these one or two bladders and including an inflation system configured to inflate and deflate the bladders to the inflated state and the deflated state respectively according to a preconditioning treatment protocol described above. The controller is further configured to inflate these one or two bladders in incremental steps by reaching predetermined pressure levels with an optional pause at each pressure level to determine the presence or absence of heart beats in the limb. The final pressure level is identified once the absence of heart beats is detected.

In a further yet aspect of the invention, provided is a combination remote ischemic preconditioning and vascular sealing device comprising an occluding bulb configured to occlude a major artery of a subject, the bulb having an inflated state and a deflated state. The device further includes a retaining means to position and retain the occluding bulb over an arteriotomy in said major artery. The device further comprises a controller connected to the bulb and including an inflation assembly configured to inflate and deflate the bulb to the inflated state and the deflated state respectively according to a preconditioning treatment protocol described above. The controller is further configured to inflate the bulb according to a vascular sealing protocol. In another aspect of the invention, the vascular sealing protocol includes a first duration when the major artery is occluded, a second duration when blood flow in the major artery is at least partially restored and a third duration when blood flow in the major artery is completely restored.

In yet a further aspect of the invention, a device for remote ischemic preconditioning and vascular sealing is provided. The device comprises a vascular sealing subassembly with an occluding bladder configured to provide hemo stasis of an arteriotomy in a femoral artery of a subject. The device further comprises a preconditioning cuff configured to retract about a thigh of the subject and including a cuff bladder incorporated therein having an inflated state to reduce blood flow in the thigh and a deflated state. The device further comprising an attachment means between the sealing subassembly and the preconditioning cuff to position and retain the occluding bladder over the arteriotomy. In a further aspect of the invention, the attachment means having a first state to position the deflated sealing bladder about the preconditioning cuff and a second state to extend the occluding bladder to the arteriotomy. In another aspect of the invention, the device further includes a controller configured to inflate and deflate the preconditioning cuff according to the treatment protocol as described above and further adapted to inflate and deflate the occluding bladder according to a vascular sealing protocol. In a further aspect of the invention, the vascular sealing protocol includes detection of at least one of complete artery occlusion condition, partial flow condition and full flow condition by monitoring pressure in a partially inflated bladder of a preconditioning cuff.

In yet another aspect of the invention, an introducer sheath is provided including a hub with a sheath tubing extending therefrom, the introducer sheath configured to be insertable into a blood vessel and further including an expandable balloon positioned on the tubing and defining an inflated state to reduce or occlude blood flow in the blood vessel of a subject and a deflated state, the sheath further including an inflation lumen connected to said balloon. In a yet further aspect of the invention, the introducer sheath further includes a controller to inflate and deflate the balloon to the inflated state and the deflated state respectively according to a preconditioning treatment protocol including a plurality of treatment cycles, each cycle comprising balloon inflation, an ischemic duration, balloon deflation, and a reperfusion duration. In a further aspect of the invention, the introducer sheath includes a blood pressure indicator comprising an air chamber with a visible window and a blood pressure lumen extending therefrom to an opening located in the artery adjacent to the balloon.

BRIEF DESCRIPTION OF THE DRAWINGS

A more complete appreciation of the subject matter of the present invention and the various advantages thereof can be realized by reference to the following detailed description in which reference is made to the accompanying drawings in which.

SINGLE-BLADDER DEVICE FOR REMOTE ISCHEMIC PRECONDITIONING

To facilitate prompt patient care and reduce ischemic damage, remote ischemic preconditioning may be initiated at the first signs of AMI. At the same time, care should be taken to assure reperfusion within about two hours following the completion of the preconditioning treatment protocol as its efficacy may be reduced thereafter. The first contact by a medical professional with a subject suffering an AMI can occur in the Emergency Department or when paramedics arrive at the subject's location. Once a preconditioning device is placed on an upper arm (or a leg) of the subject and the preconditioning treatment is initiated, it may take 3-4 cycles of about 3-5 min inflation and 3-5 min deflation intervals for the procedure to be completed, making the entire treatment occurring over 30 to 40 min period of time. Importantly, during that time, the subject may be delivered by the ambulance to the Emergency Department of hospital and then further moved to a cathlab or a surgical suite. Leaving the preconditioning device on the patient throughout moving the subject from one hospital department to the next presents a logistical problem as the ambulance personnel has to leave the preconditioning device behind with each subject or alternatively notify the next medical person of the stage of preconditioning treatment.

Figure 1:
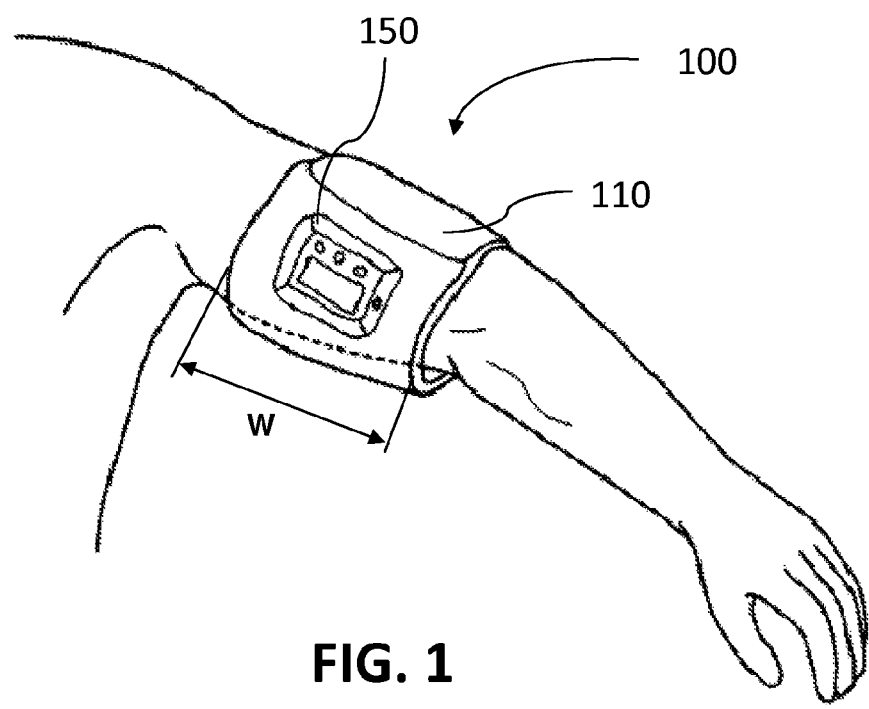
FIG. 1 is a general illustration of the device of the present invention.

FIG. 1 illustrates a general illustration of the preconditioning device 100. It includes a cuff 110 and a controller 150 incorporated therewith. Either the cuff or the controller may be made disposable or reusable. FIG. 1 shows one particular version of the device in which the controller 150 is battery-powered and integrated with the cuff. The entire device is designed for a single-time use. The novel device of the invention may be a low-cost all-in-one disposable cuff with an integrated controller. It is designed to be placed as one piece on the subject's upper arm or a thigh. The device may be advantageously designed to automatically conduct a remote preconditioning treatment protocol with a push of a single START button. No additional components of the device have to be placed elsewhere or supported at a location other than the arm or a thigh of a subject. This configuration is advantageous for use in emergency circumstances described above such as with a subject suffering from an acute heart attack, acute stroke, or acute trauma. In these situations, an all-in-one disposable automatic device is preferred because it allows for easy and rapid subject transfer during the course of preconditioning treatment from ambulance to emergency department and then to another department in the hospital. Because of its simplicity and automatic nature, there is no need to have a dedicated person to stay with the patient throughout the preconditioning treatment to ensure its proper timing. There is also no need to track and retrieve reusable components of the device after the treatment is complete—the entire device is simply disposed of after the procedure is finished. Another advantage of a fully disposable device is that it can be easily provided in sterile condition—this is advantageous for treating or pre-treating patients undergoing various surgery or percutaneous interventions.

According to other embodiments of the invention, controller 150 may be located at a location other than the cuff: it can be a stand-alone unit or be a part of a comprehensive multipurpose medical apparatus such as for example a comprehensive vital signs monitor.

The cuff 110 of the device includes or incorporates a bladder 112 (FIGS. 1 and 4) of a generally rectangular shape. Dimensions of the cuff and bladder may generally follow the standards established for blood pressure measurement cuffs, as described for example in the article by Pickering T G et al. entitled "Recommendations for Blood Pressure Measurement in Humans and Experimental Animals. Part 1: Blood Pressure Measurement in Humans", *Hypertension* 2005; 45:142-161. Another publication defining standard cuff sizes is an article entitled "Human Blood Pressure Determination by Sphygmomanometry" published by American Heart Association, 1993. Both articles are incorporated herein in their entirety by reference. In particular, the standard cuff may have a bladder length that is 80% and a width that is about 40% to 46% of arm circumference (a bladder length-to-width ratio of about 2:1). The recommended standard cuff sizes are: for arm circumference of 22 to 26 cm—the cuff should be "small adult" size, 10-12 cm wide by 22 cm long; for arm circumference of 27 to 34 cm—the cuff should be "adult" size, 13-16 cm wide by 30 cm long, for arm circumference of 35 to 44 cm—the cuff should be "large adult" size, 16 cm wide by 36-38 cm long, and for arm circumference of 45 to 52 cm—the cuff should be "adult thigh" size, 16-20 cm wide by 42 cm long.

One advantage of having the cuff and the bladder for the device of the invention having the standard sizes shown above is that the device may include an optional side port (not shown) which can be attached to a manual or automated blood pressure measurement device such as a patient monitor. The device of the invention may in that case be additionally used for manual or automatic standard blood pressure measurement before, during, or after the preconditioning treatment protocol. The controller may also be optionally adapted to allow this side port to be connected with the cuff bladder only during the reperfusion duration so as not to interfere with the efficacy of the preconditioning treatment protocol when the cuff is in the inflated state during the ischemic duration interval. The details of such device are disclosed in the above cited '536 and '038 provisional patent applications.

At the same time, as described above, there is a need to have an ischemic preconditioning device allowing for effective preconditioning treatment at the lowest possible cuff pressure applied during the ischemic duration interval. This may be achieved by utilizing the observation that the pressure needed for occluding the limb and reducing most or all blood flow through the limb (called herein a limb occlusion pressure) depends on a number of factors and does not necessarily have to be greater than the systolic blood pressure of the subject. Limb ischemia sufficient for ischemic preconditioning purposes is produced when the blood flow through the limb is at least substantially reduced or preferably entirely stopped. A reduction of about 90% or greater is believed to be sufficient to cause therapeutic effects of ischemic preconditioning. For the purposes of this description, the term "limb occlusion" encompasses limb conditions when the blood flow therethrough is reduced by at least 90% or more. The term "limb occlusion pressure" is used herein to define the condition of limb occlusion as explained above.

According to one aspect of the invention, in order to define the limb occlusion pressure to be at or below the systolic blood pressure of the subject, the width of the cuff is selected to be at or greater than about ⅓ of the arm circumference for which the length of the cuff is appropriately selected. Given the standard ranges of cuff sizes, the width of the cuff may be selected to be as follows: small adult—at least 9 cm, adult—at least 12 cm, large adult—at least 15 cm, and adult thigh—at least 18 cm.

Blood pressure monitors are known to measure blood pressure with a certain small measurement error, typically a few millimeters of mercury. To avoid partial limb reperfusion when the systolic blood pressure is measured inaccurately, the cuff of the device is provided with a width sufficient to assure a limb occlusion pressure to be well below the systolic blood pressure of the subject, typically by 5-10 mmHg. To assure the condition of limb occlusion when the cuff is placed in a minimum limb occlusion state (defined by a cuff pressure to be about or greater than the limb occlusion pressure but not exceeding the systolic blood pressure of the subject), the width of the cuff may be increased by at least 3 cm or preferably 5-10 cm as compared to the above stated standard widths. The ratio of width to arm circumference for one configuration of the device is selected to be about 0.4 or greater. In another configuration, the width to arm circumference ratio is at or above 0.5. Given the standard sizes of the cuff described above and taking into account the preference to make them wider to reduce limb occlusion pressure but without exceeding the length of the limb, the widths of the cuffs of the device are as follows: small adult—12-19 cm, adult—16-22 cm, large adult—16-25 cm and adult thigh—20-25 cm. Cuff lengths are selected to match that of standard cuffs as described above.

For example, making the cuff width at 15 cm for a small adult cuff and 18 cm for an adult cuff would define the limb occlusion pressure to be equal to a sum of $0.6\,P_{SYS}+0.4\,P_{DIA}$. Given a typical blood pressure of 110 mmHg over 80 mmHg, using such cuff will result in a limb occlusion pressure being about 98 mmHg. Maintaining the cuff pressure at a minimum limb occlusion state from about 98 mmHg to about 110 mmHg will produce limb occlusion at a reasonably comfortable cuff pressure for the subject.

Calculations for large adult and adult thigh are slightly different. In a typical example, making the large adult cuff 21 cm wide and adult thigh cuff 25 cm wide would define the limb occlusion pressure to be equal to a sum of $0.7\,P_{SYS}+0.3\,P_{DIA}$. Given the same typical blood pressure of 110 mmHg over 80 mmHg, using such cuff will result in a limb occlusion pressure being about 101 mmHg—still providing a wide enough margin for a pressure range of the minimum limb occlusion pressures of the cuff.

The central processing unit of the controller 150 may be programmed to cause the cuff inflation system to bring the cuff to the minimum limb occlusion state at least once or, in other embodiments, on a periodic basis (such as for example every minute or so) during at least a portion of the ischemic duration of the preconditioning treatment protocol. To further reduce pain and discomfort of the subject, the controller 150 may be programmed to maintain the cuff pressure between the limb occlusion pressure and the systolic blood pressure of the subject throughout the entire ischemic duration interval.

To achieve this objective, it is important to accurately and frequently detect the value of the systolic blood pressure of the subject. The device of the invention is devised to provide for such accurate and frequent determination of the systolic blood pressure while the cuff is placed in the minimum limb occlusion state. One advantage of the device of the invention is that the systolic blood pressure may be determined frequently but without compromising limb occlusion and therefore jeopardizing the therapeutic effect of the ischemic preconditioning.

Figure 2:
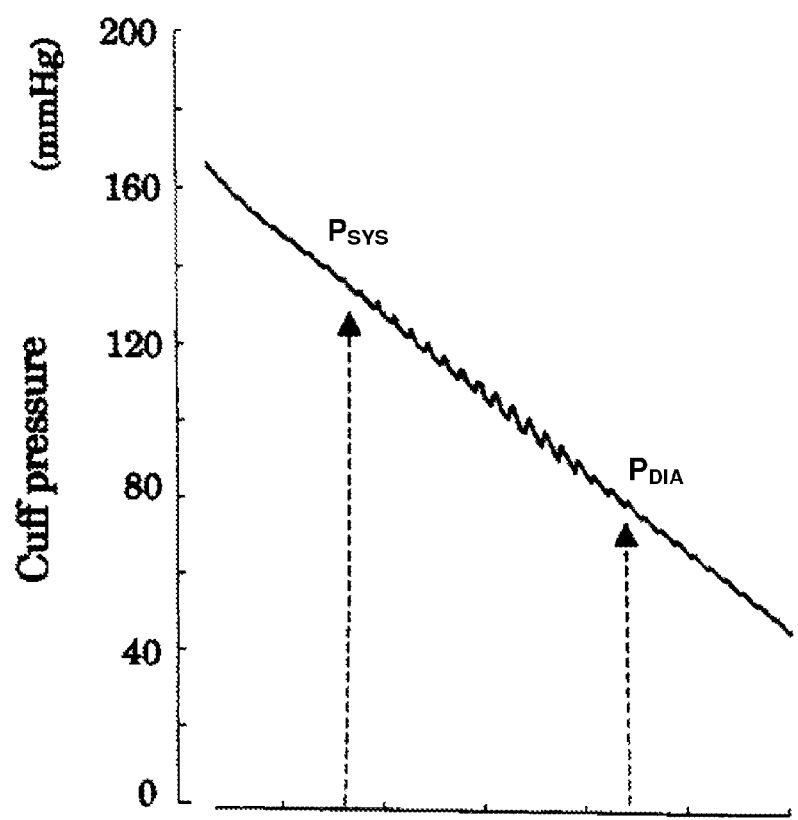
FIG. 2 is a general chart of cuff pressure used in a traditional oscillometric method of measuring blood pressure disclosed in the prior art.
Figure 3:
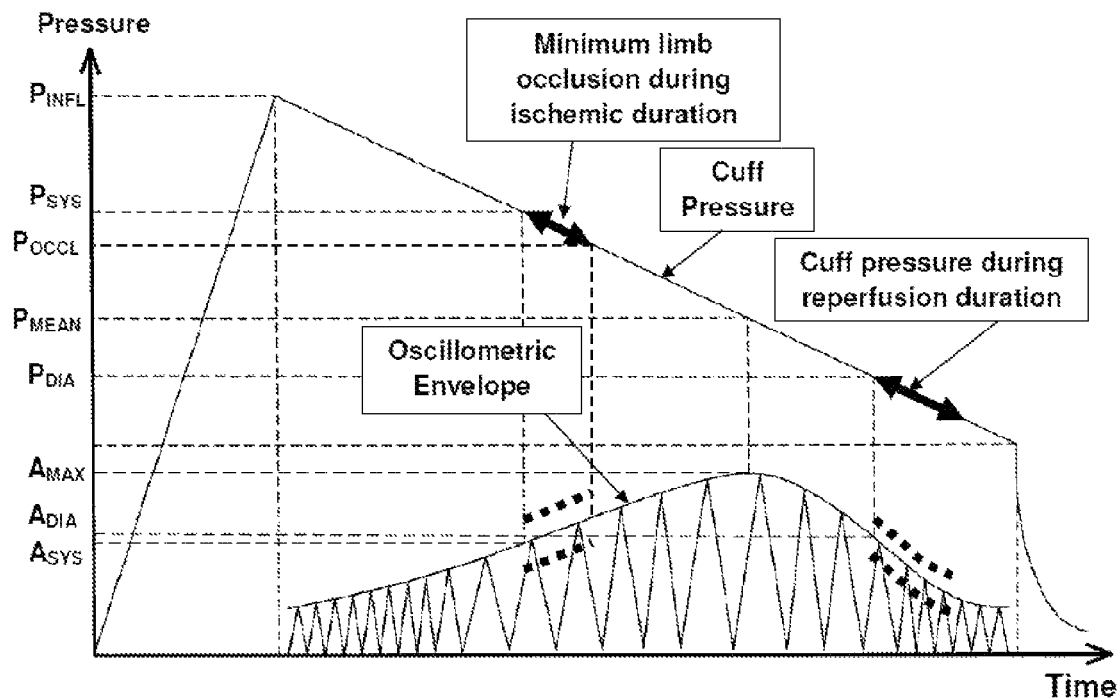
FIG. 3 is a chart illustrating measuring systolic blood pressure and inflating/deflating the cuff of the device during the preconditioning treatment protocol of the invention.

One proposed method of detecting and frequently updating the value of systolic blood pressure of the subject is based on a novel modification of oscillometric method of blood pressure measurement. Traditionally, during the oscillometric blood pressure measurement, the cuff is inflated to a pressure above the previously measured or estimated systolic blood pressure of the subject. The cuff is then gradually deflated with a deflation rate of 2-5 mmHg per second while the controller is configured to record the cuff pressure. FIG. 2 contains a typical recording of cuff pressure during the procedure of blood pressure measurement. Increased pulsations are observed on the cuff pressure curve in the area generally between the values of systolic and diastolic blood pressures. The principles of oscillometric determination of blood pressure are explained in detail in the prior art publications, for example in an article by G. Drzewiecki et al. entitled "Theory of the oscillometric maximum and the systolic and diastolic detection ratios", Annals of Biomedical engineering, 22:88-96, 1994 incorporated herein in its entirety by reference. Cuff pressure pulsations are extracted from the cuff pressure curve and converted into a separate curve of pulsation amplitude vs. time. This curve is referred to as an oscillometric envelope. Typically, as the cuff pressure is being gradually reduced, the amplitude of cuff pulsations is increasing once the cuff pressure is below systolic blood pressure of the subject. The amplitude of pulsations reaches a maximum at a mean arterial pressure and then gradually declines past the point of diastolic blood pressure. One typical example of an oscillometric envelope is shown in FIG. 3. Recording a full oscillometric envelope allows measuring of the mean arterial pressure at the cuff pressure curve at the point corresponding to $A_{MAX}$ which is the maximum amplitude of the oscillometric envelope curve. The values of systolic and diastolic blood pressures are then determined using empirically-derived predetermined ratios. The maximum amplitude $A_{MAX}$ is multiplied by a systolic ratio of about 0.55 and the amplitude point $A_{SYS}$ on the oscillometric curve where the amplitude is that of 0.55 times $A_{MAX}$ is used to look up the cuff pressure which is then declared to be a systolic blood pressure of the subject. Diastolic blood pressure is determined at the amplitude point of $A_{DIA}$ where the amplitude of pulsations is that of $A_{MAX}$ multiplied by a diastolic ratio of about 0.85—see FIG. 3.

Recording cuff pressure may be done using a pressure sensor and extracting a full oscillometric envelope from the signal derived therefrom. This may be done on gradual cuff deflation or gradual cuff inflation. Using cuff deflation method allows an advantage of a pressure signal not contaminated by the noise introduced by an air pump. On the other hand, using cuff inflation method allows not overinflating the cuff beyond the systolic blood pressure. Both cuff inflation and cuff deflation methods may be used for the purposes of this invention.

As can be readily appreciated by those skilled in the art, blood pressure of a subject may change from time to time. In critically-ill patients, blood pressure may fluctuate significantly over relatively short periods of time such as minutes or even seconds. Heart attack or stroke patients may slip into a cardiogenic shock if the blood pressure falls below a certain minimum safe value. Rapid detection of falling blood pressure is important for proper management of such subjects so that corrective measures are taken as quickly as possible. As both systolic and diastolic blood pressure values are typically falling in circumstances of hemodynamic deterioration, it may be possible to frequently monitor only a systolic or diastolic value in order to detect an event of falling blood pressure. According to the present invention, a LOW BLOOD PRESSURE alarm is initiated when either the systolic or diastolic blood pressure is detected to be below their corresponding predetermined low level thresholds. For systolic pressure, this low level threshold may be designated for example to be between 50 and 70 mmHg, while for diastolic blood pressure that low level threshold may be for example between 30 and 50 mmHg. The alarm is triggered when either of these thresholds is crossed. In addition to detecting rapidly falling blood pressure, it is important to detect rising blood pressure as it may among other consequences compromise the limb occlusion state. Upper limits for systolic and diastolic blood pressures may also be provided and a HIGH BLOOD PRESSURE alarm may be triggered when either the systolic or diastolic blood pressure has exceeded its corresponding high pressure threshold. Heart rate monitoring may also be optionally displayed while detecting the subject's blood pressure.

Using a traditional method of measuring blood pressure requires detecting the maximum amplitude of pulsations of the oscillometric envelope. This in turn requires deflating the cuff at least through a point of the mean arterial pressure. Doing so during the ischemic duration interval will allow for at least partial reperfusion of the limb. To avoid this detrimental effect, the present invention provides for various new methods of detecting systolic blood pressure without deflating the cuff below the limb occlusion pressure.

According to one method of the invention, an initial recoding of the full oscillometric envelope is made covering the pressure range from below the diastolic pressure to above the systolic pressure of the subject. This can be done during the cuff inflation interval or a cuff deflation interval in one or several of the preconditioning treatment protocol cycles or at other times. The values of $A_{MAX}$, $A_{SYS}$, and $A_{DIA}$ are determined and so are the values of systolic and diastolic pressures. Limb occlusion pressure is then determined using the known cuff width and length, for example using the following equation: $P_{OCCL} = P_{DIA} + (P_{SYS} + P_{DIA}) \times C/(3 \times W)$, where C is limb circumference and W is bladder width.

The cuff is then inflated by the cuff inflation assembly of the controller to an inflated state to initiate the ischemic duration interval. One method of the invention is based on the assumption that when the blood pressure generally rises or falls, both systolic and diastolic pressures go up or down. The spread between the systolic and diastolic values may increase when the blood pressure generally goes up or it can decrease as the blood pressure of the subject generally falls down. Frequent surveillance of only either a systolic or diastolic blood pressure may therefore be used for making a reliable judgment as to whether subject's hemodynamics is compromised or not.

During the ischemic duration interval, the current value of systolic blood pressure of the subject may be determined at least one time during the ischemic duration interval. In other embodiments, it is determined several times or on a periodic basis. The frequency of such determination of systolic blood pressure may be about once every minute, once every 30 seconds or even more frequently. In another embodiment of the invention, systolic blood pressure is monitored continuously during at least a portion or preferably the entire ischemic duration interval. Systolic blood pressure is determined by bringing the pressure in the cuff to about the previously detected value of systolic blood pressure but not reducing it to the value lower than that of the limb occlusion pressure so as not to compromise limb occlusion. The electronics of the controller may be programmed to operate the cuff inflation assembly to bring the cuff pressure to a vicinity of a previously recorded systolic blood pressure. A continuously updated segment of the oscillometric envelope is thereby recorded and compared with the previously obtained curve as the cuff pressure is adjusted by the controller—see FIG. 3 dotted lines. The new curve may be above, at or below the initially recorded full oscillometric envelope curve or a previously recorded segment thereof. Since the new segment is recorded within a short time after the previous recording, the blood pressure measurement circumstances do not change appreciably to introduce a significant measurement error. Only the changing blood pressure may be assumed to cause the shift in the oscillometric envelope curve. If the curve is found to be close (within a predetermined margin of error) to the initial previous curve, the controller is programmed to not change the previously recorded values of systolic (and optionally diastolic) blood pressure. The oscillometric curve is being monitored by the controller in real time. If the curve is detected to shift up or down, the cuff is continued to be deflated (or inflated) by the controller only until about the point where the pulsations amplitude is equal with the previously recorded $A_{SYS}$ and a correction calculation may be initiated. The correction calculation includes determining that cuff pressure at which the amplitude of the oscillometric curve is the same as previously detected $A_{SYS}$, which pressure is then designated as the new value of systolic blood pressure. The correction also involves recalculating limb occlusion pressure and optionally diastolic pressure of the subject. In one embodiment, the new limb occlusion pressure may be calculated as the new value of systolic blood pressure minus the previously known difference between the previous systolic blood pressure and the previous limb occlusion pressure. In another embodiment, the new limb occlusion pressure is calculated based on the equation above and the new estimated value of diastolic blood pressure. The new estimated diastolic pressure may be calculated using predetermined values or slopes for the increase or decrease of the spread between the systolic and diastolic pressures of the subject with a corresponding increase or decrease in the systolic pressure. Both systolic and diastolic pressures (and optionally a mean arterial pressure and a heart rate) may be shown on a display of the device or transmitted to a conventional display of a patient monitor. The next round of varying or dithering cuff pressure is done around the newly calculated values. Shifting of the curve segment upwards indicates an increase in blood pressure while shifting downwards indicates a drop in blood pressure of the subject.

The above described method needs periodic re-calibration by recording a new full oscillometric envelope curve. During the preconditioning treatment procedure, full inflation and deflation of the cuff is scheduled at the beginning and the end of every ischemic duration interval and reperfusion duration interval, which occur every 3-5 min. These events represent convenient opportunities to refresh the full oscillometric envelope. In one method of the invention, full recording of oscillometric envelope may be done only during cuff inflations or during cuff deflations. In another method of the invention, full oscillometric envelope may be recorded on both cuff inflations and cuff deflations so as to minimize the time period between such recordings. In yet other embodiments of the invention, once the LOW or HIGH blood pressure thresholds are crossed by either the systolic or diastolic blood pressures, the preconditioning treatment protocol is automatically interrupted, an alarm is activated and a full recording of oscillometric envelope is conducted to confirm the present value of both diastolic and systolic blood pressure of the subject.

Diastolic blood pressure of the subject may be periodically detected using a similar technique as described for systolic blood pressure but during the reperfusion duration. At least once (or in other embodiments on a periodic basis such as about every 30 or 60 seconds), the pressure in the cuff is raised to about the previously detected or estimated value of the diastolic blood pressure. The new value of diastolic blood pressure may be detected by matching the amplitude of the newly recorded segment of the oscillometric envelope with the previously recorded $A_{DIA}$. An upwards shift of the oscillometric envelope segment (shown as dotted line in FIG. 3 in the zone of diastolic pressure) indicates a drop in diastolic and likely a systolic blood pressure of the subject. A downward shift indicates an increase in blood pressure of the subject. Once the new value of diastolic blood pressure is detected, an updated value of the systolic blood pressure may be calculated and both pressures may be then shown on a display.

Safe ranges of allowable systolic and diastolic blood pressures are preselected to trigger a LOW BLOOD PRESSURE or HIGH BLOOD PRESSURE alarms if either the systolic or diastolic blood pressures falls outside these respective safe ranges. Using the above described methodology allows a near-continuous monitoring of the subject's blood pressure before, during and/or after the completion of ischemic preconditioning treatment. Monitoring of systolic blood pressure during the ischemic duration interval coupled with monitoring diastolic blood pressure during reperfusion duration provides for uninterrupted hemodynamic surveillance throughout the preconditioning treatment protocol. This is advantageously done on the same limb, with minimal occlusion of the limb tissue, and without compromising the efficacy of the preconditioning treatment itself.

In another embodiment of the invention, detecting systolic and diastolic values from the segments of the oscillometric envelope recorded in the vicinity of previously detected systolic and diastolic values is done by providing the controller with a program for analyzing the first derivative of these segments. A maximum of the first derivative of the systolic segment indicates a cuff pressure at the systolic blood pressure of the subject, while the minimum of the first derivative of the diastolic segment of the oscillometric envelope may be used to indicate the current value of the diastolic blood pressure. This method may be used by itself or in combination with the above or below described methods to increase the accuracy of detecting systolic and diastolic blood pressure values.

Bringing the cuff to a minimum limb occlusion state allows detection of systolic blood pressure by means and methods other than described above which are based on pure oscillometry. For example, a sensor such as a microphone or a liquid-filled balloon may be incorporated in the cuff of the device of the present invention for monitoring of Korotkoff sounds. Once the sounds are detected, a new value of systolic blood pressure may be established. The same sensor may be applicable to detecting diastolic blood pressure by cessation of Korotkoff sounds during the periods of cuff deflation and limb reperfusion. Other sensors may also be used for this purpose such as for example a plethysmograph sensor, a Doppler sensor, etc.

Figure 4:
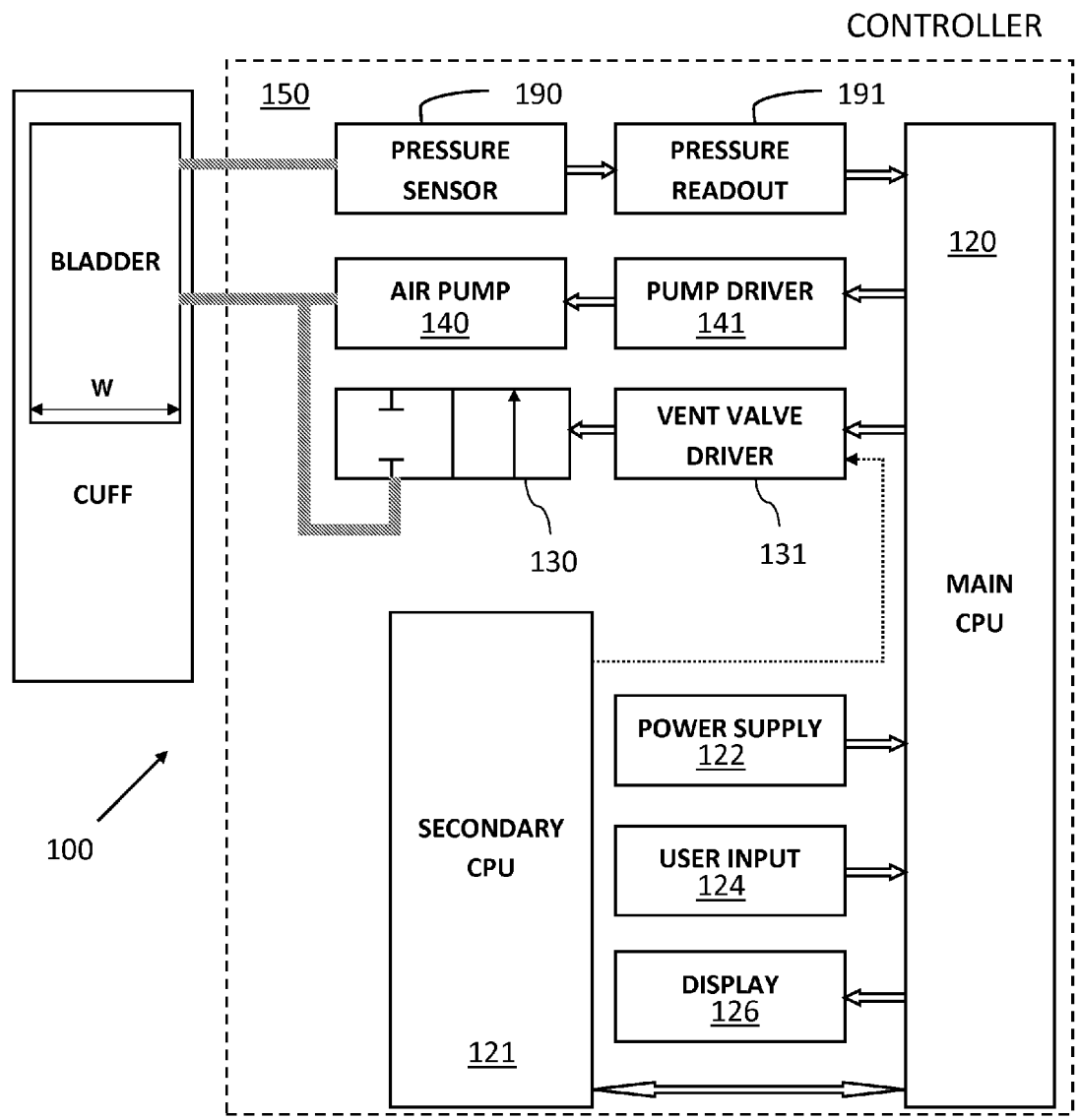
FIG. 4 is a block-diagram of the device according to one aspect of the invention.

The controller 150 suitable for the purposes of the present invention is schematically illustrated in FIG. 4. It includes a number of air handling elements cumulatively forming a cuff inflation assembly and operable by a central processing unit 120, preferably ASIC-based. The cuff inflation assembly includes an air pump 140 which may be for example a diaphragm pump or an air turbine driven by an electrical motor. Other sources of compressed air or gas may be used for the present invention. For example, a cartridge containing compressed air or carbon dioxide may be used in an all-disposable version of the device. Compressed gas may also be obtained as a result of a controlled chemical reaction, components for which may be stored in a sealed container prior to use of the device. Wall compressed air may be used on the other hand for a wall-mounted version of the device, such as when used in the hospital. In other embodiments, when the device is a part of a comprehensive patient monitor, its air supply may be adapted to provide compressed air for the device. In a semi-automatic or a manual version of the device, a manually-operated pump such as a compression bulb may be used to produce compressed air. Yet, in further embodiments, pressurized liquid may be used to inflate and deflate the bladder of the device.

The air pump 140 may be sized to provide a slower rate of cuff inflation as compared with traditional blood pressure measuring devices, which are typically designed to complete the act of inflating the blood pressure cuff as quickly as possible, frequently in about 10 seconds or less. Traditional blood pressure monitors are designed to finish the procedure of taking a blood pressure reading as quickly as possible so as to rapidly provide the reading to the medical practitioner—necessitating fast inflation of the cuff. Another reason for rapid inflation is to avoid measurement errors caused by motion of the subject.

The remote ischemic preconditioning device of the invention may not be concerned with these objectives and can be allowed to complete the inflation of the cuff over a longer period of time such as 20, 30, 40 seconds or even longer. Slower rate of inflation (preferably less than about 0.1 cubic foot per minute) makes it possible to significantly reduce the size and weight of the air pump 140, the pump driver 141, and the batteries of the power supply 122 needed for its operation. In one embodiment of the invention, components traditionally sized for use in wrist blood pressure monitors can be used for inflating the cuff of the present invention, which is sized for use with an upper arm of the subject.

Another advantage of slow inflation is that reliable detection of the oscillometric curve may be less difficult during cuff inflation when air is introduced into the cuff at a slower rate. Variable rate of cuff inflation is also contemplated by the present invention: high cuff inflation rate (such as for example over about 0.1 cubic foot per minute) may be used initially and low cuff inflation rate (such as for example less than about 0.1 cubic foot per minute) may be used when the cuff pressure reaches blood pressure measurement zones, such as in the vicinity of systolic, mean, and diastolic pressures.

Other elements of the cuff inflation assembly include the pressure sensor circuit comprising a pressure sensor 190 and the pressure readout unit 191. A vent valve 130 with its driver 131 is provided to vent the cuff bladder to atmosphere. A fast rate of venting or a slow rate of venting may be provided by the vent valve 130 at different times during the procedure of measuring blood pressure. One technique useful for adjusting the rate of venting is pulse-with-modulation of the valve—the valve may be rapidly opened and closed with adjustable frequency so as to permit variable rate of air therethrough. Fast venting rate may be advisable during cuff deflation intervals, while slow rate of venting may be used during a pressure measurement procedure. Two separate valves may also be used for this purpose—a large-bore valve for fast rate venting and a small-bore valve (or a valve connected to a predefined air flow restrictor) may be used for slow rate venting.

The cuff inflation assembly may be operated by a main central processing unit 120, which may in turn be further supplemented by a secondary CPU 121. The main function of the secondary CPU 121 may be to monitor the performance of the main CPU 120 and assure proper opening and closing of the vent valve 130. In case of a malfunction of the main CPU 120, the secondary CPU 121 may be programmed to open the vent valve 131 (dotted line in FIG. 4) to ensure subject's safety.

Other parts of the electronic portion of the controller 150 include the power supply 122, the user input 124, and the display 126. When the device of the invention is incorporated into other devices such as a comprehensive patient monitor, these elements and their functions may be provided by corresponding elements of the patient monitor. In case of a dedicated controller configured for preconditioning and pressure monitoring function of the stand-alone version of the present invention, the power supply 122 includes batteries, preferably primary lithium batteries with long shelf time. Wall outlet power or rechargeable batteries are also contemplated as useful energy sources.

When the controller 150 is operated properly during the course of the ischemic preconditioning treatment protocol, the main CPU 120 is programmed to start, adjust the speed and stop the electrical motor operating the air pump 140; cause properly timed opening and closing of the vent valve 130 via operating a vent driver 131; and to record and process the pressure signal using the pressure sensor 190 and the pressure readout unit 191. All these operations are cumulatively referred to by the terms "inflating the cuff", "deflating the cuff", or "bringing the cuff to a certain pressure" as used above and below throughout this description.

In one useful configuration of the device, the user input 124 is a single START button. In a fully automatic version of the device, once the cuff is placed about the limb of the subject, pushing this button may start the ischemic preconditioning treatment protocol so no further action is required from the user. Progression of the treatment may be communicated to the user by a display 126. Other user input buttons that may be optionally provided including an "Emergency deflate" and "Resume" buttons. These buttons are useful to allow the medical practitioner to interrupt the treatment protocol. The functionality of these buttons may also be designed into the above mentioned START button. For example, depressing and holding the START button during the treatment may interrupt it. Pressing it again after such interruption will cause the protocol to be resumed. The controller 150 may be configured in this case to resume the interrupted cycle from the beginning or repeat the entire treatment protocol if the interruption delay has been longer than allowed, such as for example 10 min or more. One advantage of designing these functions into the START button is to make the user interface as simple as possible by only providing dedicated buttons for frequently used functions, such as a single START button for example.

The main CPU 120 and display 126 of the controller 150 may additionally be programmed to start a 1- or 2-hour countdown at the end of the ischemic preconditioning treatment protocol. As the first window of ischemic preconditioning effect has limited duration of 1-2 hours, it is critical to restore blood flow to the ischemic organ within that general period of time. The display may include a time countdown segment to advise the user of progression of that time period. If reperfusion of the ischemic organ is not accomplished within that timeframe, the treatment may have to be repeated later and completed preferably just prior to expected reperfusion of the ischemic organ. One situation when this may be the case is when a heart attack patient is brought to the first hospital which is not equipped for percutaneous interventions. A transfer to the second hospital having such capability may cause a prolonged delay. The device of the invention may be configured to allow for a second ischemic preconditioning treatment, which may be timed to be completed at the time of arrival to this second hospital or shortly thereafter.

A disposable version of the device of the invention may be further configured to limit the number of operating hours or the number of treatments the device is allowed to deliver so as to prevent further use and ensure the proper function of the batteries. Initial activation of the device may be accomplished by pulling out a tab to connect batteries to the controller 150. Once activated, the device may be limited as to how long it stays active using one of the protocols as described below:

- Up to about 40 min for one 4-cycle procedure—device may be permanently disabled thereafter and only allowed to support a 2-hour reperfusion countdown on its display;
- 40 min+2 hours reperfusion countdown+40 min+2 hours countdown for two ischemic preconditioning treatments back to back;
- 40 min+2 hours countdown+up to 10 hours of stand-by+40 min+2 hours countdown for two procedures—useful when the first procedure and the first 2-hour window did not result in reperfusion, the second procedure may be done up to 10 hours later and just before the second reperfusion attempt (example—transfer of patient to a second hospital);
- Up to 12 or 24 hours fixed operational time—allows using the device both prior and past the PCI or thrombolysis procedure for delivering one or several preconditioning treatment protocols before and after the reperfusion of the ischemic organ.

Other optional features may include a manual user input capability to enter a user-selected limit of cuff inflation pressure. If the device cannot detect the blood pressure of the subject, an override may be included allowing the user to select the upper level of cuff inflation. The function of the device may be limited in this case as no automatic monitoring of hemodynamics would be conducted. At the same time, the primary purpose of the device, namely providing ischemic preconditioning will still be enabled.

In another embodiment, the device of the invention may be configured to be used as a hybrid blood pressure measuring device. The user input unit 124 will in this case additionally include a SYSTOLE and DIASTOLE buttons. During the process of taking a blood pressure reading, the medical practitioner may inflate the cuff (activating the air pump 140 or manually) to a pressure above an estimated systolic pressure and then activate a slow deflation of the bladder while listening for Korotkoff sounds with a stethoscope. Once the first sound is detected, a SYSTOLE button is pressed. The device may be configured to record and display the instant pressure reading from the pressure sensor 190 at the time the SYSTOLE button is pressed as the systolic pressure of the patient. The gradual deflation of the bladder is then continued and when the last Korotkoff sound is heard, the medical practitioner presses a DIASTOLE button freezing the instant reading from the pressure sensor 190 as a diastolic pressure of the patient. The device may be then configured to rely on these blood pressure measurements to conduct the preconditioning treatment protocol as described above but without further hemodynamic surveillance.

Dual-Bladder Device for Remote Ischemic Preconditioning

Figure 5:
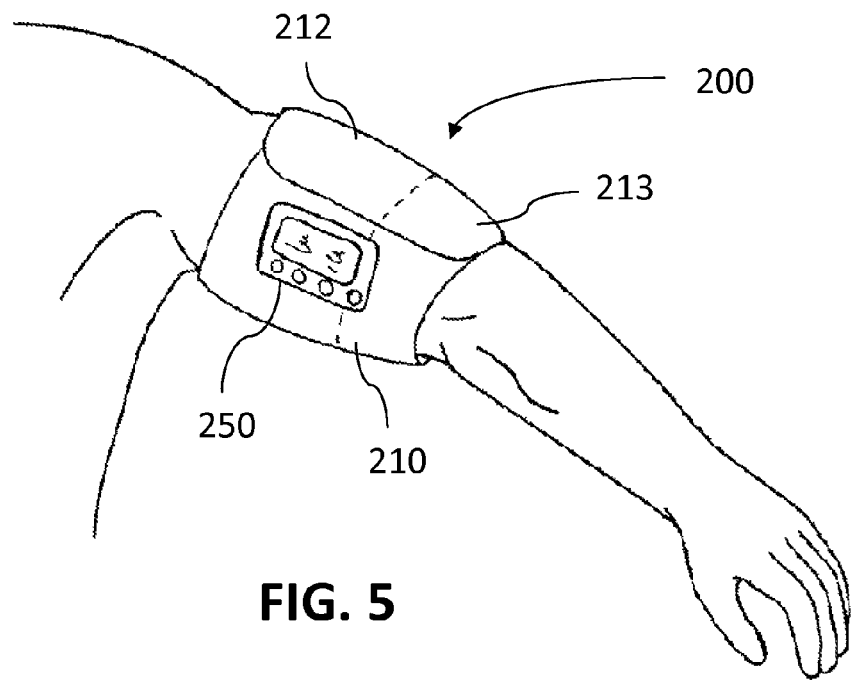
FIG. 5 is a general illustration of the preconditioning device of the invention where the cuff includes a proximal and a distal bladder.
Figure 6:
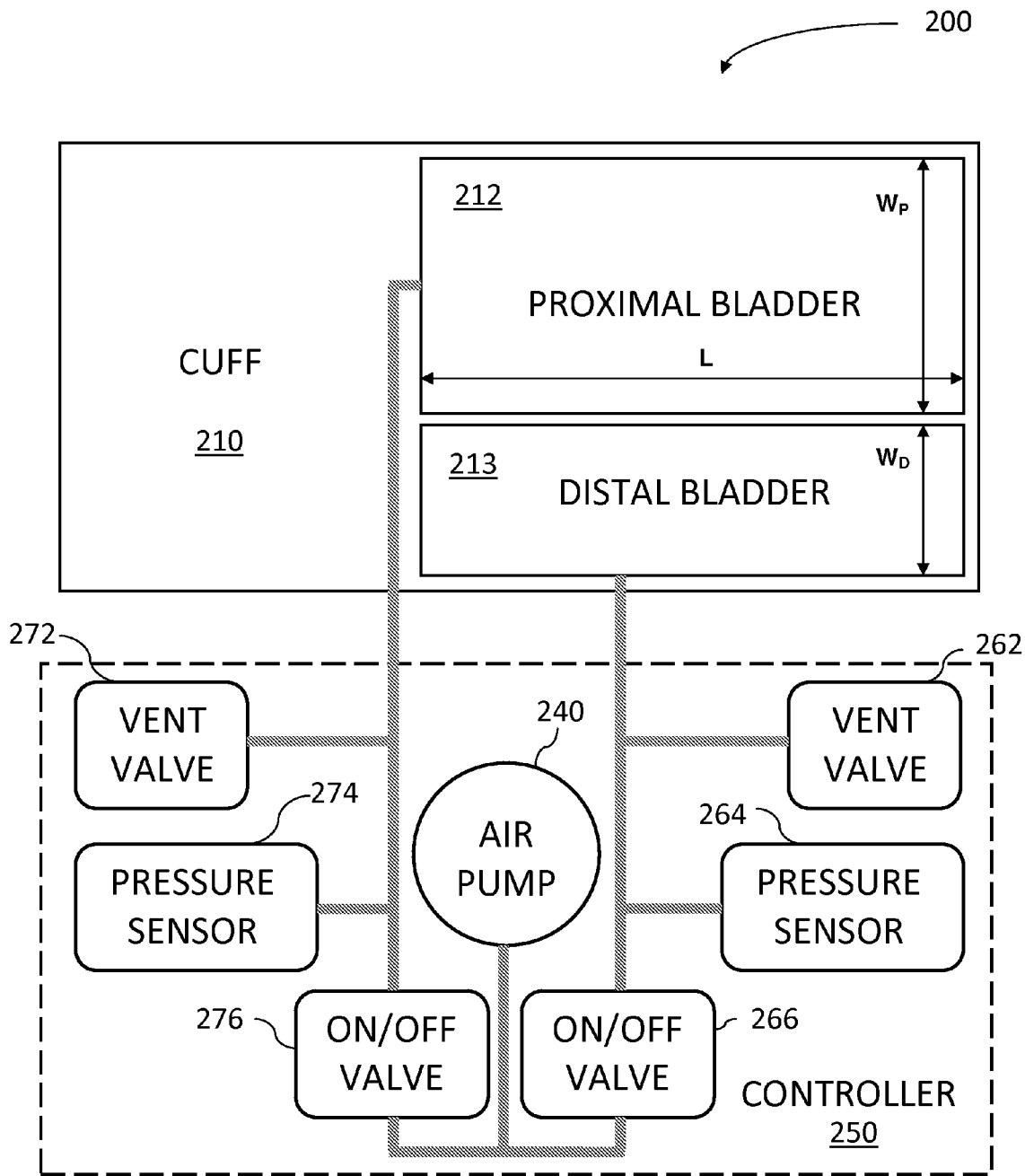
FIG. 6 is a block-diagram of the air handling elements and cuff inflation assembly of the device according to another aspect of the invention in which the device includes a dual-bladder cuff.
Figure 7:
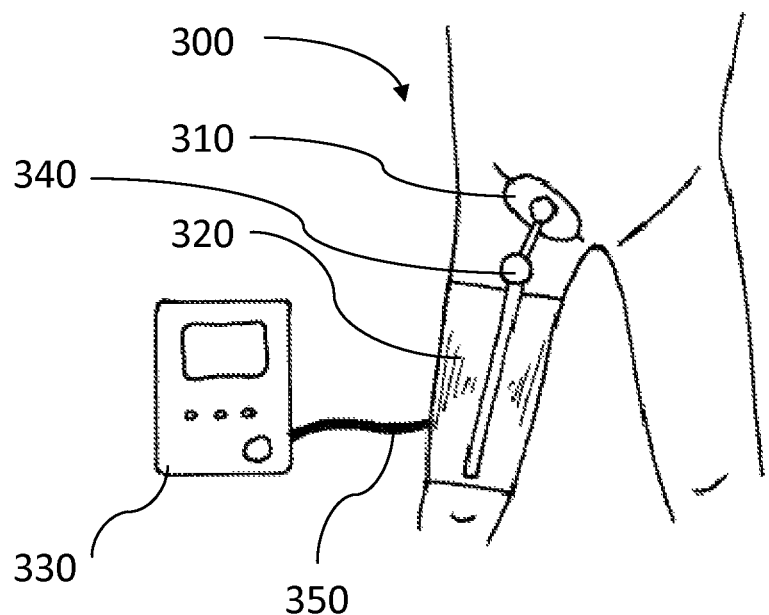
FIG. 7 is a schematic illustration of the device of the invention configured for use during a percutaneous catheterization procedure.
Figure 8:
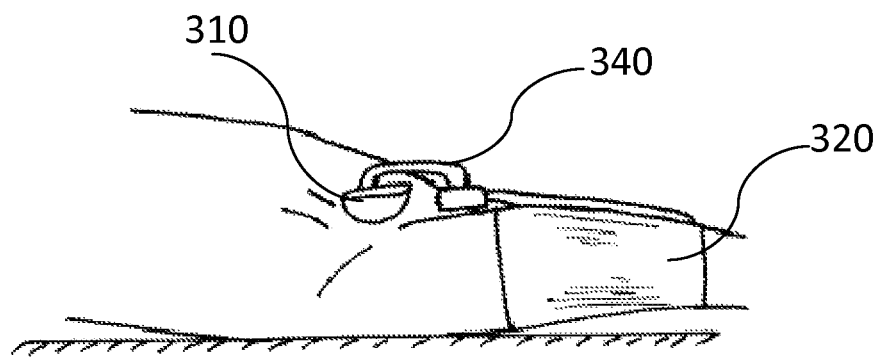
FIG. 8 is a side view of the device shown in FIG. 7.

FIGS. 5 and 6 pertain to a dual-bladder embodiment of the present invention. Having more than one bladder allows a more accurate detection of systolic and diastolic blood pressure values of the subject. When only one bladder is used, occlusion of the arterial blood flow through the limb may be primarily accomplished in the middle portion of the bladder. The upper or proximal portion of the bladder invariably has a section where the artery is only partially occluded. This causes a low level of pulsations to be still present on the cuff pressure curve even at cuff pressures above the limb occlusion pressure and even further at pressures above the systolic blood pressure of the subject. This creates a situation when complete occlusion of the limb does not entirely depress cuff pulsations making it difficult to accurately detect the level of systolic blood pressure. One way to address this problem involves using various above-described empirically-derived methods of determining systolic and diastolic blood pressure values. The limitation of these methods is that they rely on statistically-derived average ratios of pulsation amplitudes. Such average ratios may not be entirely accurate for all patients. It is desired therefore to actually measure the values of systolic and diastolic blood pressures rather than calculate them based on a measured mean arterial pressure. It is further desirable to provide these measuring methods without jeopardizing the preconditioning treatment efficacy. In other words, it is desirable to measure systolic blood pressure during the ischemic interval without allowing for reperfusion. It is also desirable to measure the diastolic blood pressure during reperfusion duration without significantly obstructing blood flow through the limb.

The cuff 210 of the dual-bladder embodiment includes a first bladder 212 (designated here as a proximal bladder—that which is closer to the heart) and an opposing second bladder 213 (designated here as a distal bladder—that which is further away from the heart). In another embodiment, both bladders are located adjacent or next to each other. To assure a snug fit over the limb of the subject, both bladders may be joined together only along a portion of their circumference. Separated ends of the cuff are envisioned to be individually wrapped about the limb of the subject to provide a tight fit over a curved limb. Inflating both bladders to a pressure at or above the limb occlusion pressure will act to substantially occlude the limb as if with a single bladder having a total width equal to the sum of widths of the proximal and distal bladder, $W=W_P+W_D$. The bladder circumference L may be also selected to be equal between the proximal bladder 212 and the distal bladder 213 so as to assure an even compression of the limb when both bladders are inflated to the same pressure. Both bladders in that sense can be viewed as two parts of a single wide bladder. The combined bladder width and bladder length of the cuff in this embodiment may follow the recommendations and sizes described above for the single-bladder embodiment of the invention.

In one aspect of the invention, while the total width of both bladders may be made to cover substantially the entire length of the limb such as the length of the upper arm, the width of one of the bladders (such as the proximal bladder 212 for example) may be made to follow standard sizing of blood pressure measuring cuffs as described above. Given the limitation of the total available length of the limb, this makes the distal bladder 213 narrower than the proximal bladder 212. Having at least one of the bladders with a standard cuff width allows using that bladder for traditional manual or automatic oscillometric blood pressure measurement. Such traditional blood pressure measurement may be used in combination with the results obtained using the methods described in this disclosure to assure its accuracy and improve its reliability. For example, when a measurement error or inability to measure blood pressure using some methods of the invention are detected by the controller of the invention, it may be configured to revert to traditional oscillometric measurement to still obtain blood pressure data.

The controller 250 is illustrated schematically in FIG. 6. Only the air handling components forming the cuff inflation assembly are shown in FIG. 6. The electronic components including the central processing unit are similar to that described above for controller 150 and therefore are not shown. Each bladder may be generally inflated and deflated via its own dedicated air handling circuit. The proximal bladder 212 may be inflated by the air pump 240 when it is connected by the controller to the bladder via activating an on/off valve 276. Gradual deflation of this bladder may be accomplished by the controller programmed to open and close at appropriate times a vent valve 272 while the pressure in the proximal bladder may be monitored by a pressure sensor 274. The distal bladder 213 may be inflated the controller opens the on/off valve 266 and activates the same air pump 240. It may be deflated by the controller by opening the vent valve 262, and monitored by the pressure sensor 264. This arrangement allows for both independent or simultaneous inflation and deflation of bladders 212 and 213. It also provides for redundancy in operation whereby increasing the safety of the device. For example, if one of the vent valves malfunctions and cannot be opened, both bladders may still be deflated by opening the other vent valve as well as both valves 266 and 276. Cross-checking or equilibrating of pressure in the bladders may also be possible by the controller causing opening of both valves 266 and 276.

Prior to, during or after the preconditioning treatment protocol, one or both bladders 212 and 213 may be used to periodically measure blood pressure of the subject. Such measurement may be taken on inflation or deflation of the bladders. Assuming measurements on cuff deflation, a novel blood pressure measurement procedure would include the controller 250 causing inflation of at least the proximal bladder 212 to a pressure exceeding a previously measured or estimated systolic blood pressure of the subject. The distal bladder 213 may then be inflated by the controller operating the cuff inflation assembly to a pressure sufficient to monitor arterial cuff pulsations caused by heart rate pulsatility. As maximum amplitude of pulsations in either bladder is expected to be detected by the controller 250 around the point of mean arterial pressure, in one method of the invention, the distal bladder 213 may be inflated to a previously measured or estimated mean arterial pressure. This pressure setting is advantageous when measuring blood pressure in subjects with weak or difficult to detect pulsations of the cuff pressure. Yet, in another method of the invention, the distal bladder 213 may be inflated by the controller 250 to the same or slightly lower pressure as that of the proximal bladder 212 so as to contribute to the overall occlusion of the limb during or after the blood pressure measuring procedure. The pressure in the proximal 212 and distal 213 bladders may then be gradually decreased by the controller 250 opening the vent valves with the distal bladder 213 having a pressure not exceeding that of the proximal bladder 212. Once the pressure in the proximal bladder 212 is at or below the level of systolic blood pressure, the amplitude of pulsations in the distal bladder 213 undergoes a rapid increase, at least by 20% or more, from the previously detected level. In some patients, this amplitude may reach 2 to 10 times that of the previous level. This rapid or sudden increase is caused by arterial pulsations no longer prevented by the proximal bladder 212 from reaching the distal bladder 213. Simultaneous or alternating pressure monitoring in both bladders allows detection of the pressure point in the proximal bladder 212 corresponding with an increase in the amplitude of pulsations in the distal bladder 213. This proximal bladder pressure may then be designated by the controller 250 as the systolic blood pressure of the subject. The pressure in the proximal bladder 212 may be optionally increased and gradually decreased again at least one or more times so as to cross the systolic blood pressure point repeatedly to collect additional measurement points. An average reading may then be calculated so as to reduce the impact of measurement artifacts. This reading may then be displayed for the user on a display of the device.

Once the systolic blood pressure is identified, continuing deflation of proximal and distal bladders may be used to detect the diastolic blood pressure. When the pressure in both bladders is between the diastolic and systolic values, the amplitude of pulsations in the proximal bladder 212 would be generally higher than pulsations in distal bladder 213 as the proximal bladder 212 would impart certain blood flow restriction and therefore dampen the magnitude of pulsations in the distal bladder 213. It is further suggested that once the pressure in the proximal bladder 212 has reached the distal blood pressure, both bladders would have pulsations of similar and reduced magnitude, as there would be no more restrictions on the blood flow through the limb. The pressure value in the proximal bladder 212 at which the amplitude of pulsations in both bladders have reached a comparable level (such as within 10% of each other) may be used as a point where diastolic blood pressure is detected. In other embodiments of the invention, the pressure in either bladder when pulsations amplitude has dropped to a predetermined level or has dropped rapidly as compared with the previous level (such as by 20% or more) may be used to indicate the diastolic blood pressure of the subject.

The general dual-bladder blood pressure measuring procedure described above may be adapted to be conducted by the controller 250 during the ischemic preconditioning treatment protocol without compromising its efficacy. At the beginning of at least one preconditioning cycle or in other embodiments at the beginning of each preconditioning cycle, both bladders 212 and 213 are caused by the controller 250 to be inflated to a pressure at or above the previously determined or estimated value of limb occlusion pressure. In one preferred method of the invention, the proximal bladder 212 may then be inflated to a pressure above that previously measured or estimated systolic blood pressure of the subject while the distal bladder 213 may be kept at a pressure between the limb occlusion pressure and the systolic blood pressure. The pressure in the proximal bladder 212 may then be gradually reduced until a sharp increase in pressure pulsations in the distal bladder 213 is detected so as to indicate the new value for systolic blood pressure. Having the new value of the systolic pressure allows calculating the new value of limb occlusion pressure using the known width and length of the cuff. Both bladders may be then inflated by the controller 250 to a pressure at least equal or above the newly calculated limb occlusion pressure and optionally close to or higher than the newly detected systolic blood pressure. Periodic repeating of systolic blood pressure detection procedure may be used for hemodynamic surveillance. Periodicity of repeating the blood pressure determination procedure may be at least once during each ischemic duration interval. In other embodiments, systolic blood pressure is measured once about every 30 to 60 seconds. In yet another embodiment of the invention, the pressure in the proximal bladder 212 may be continuously adjusted or dithered by the controller to fluctuate about the systolic blood pressure so as to monitor its change essentially on a continuous or near-continuous basis. This approach has an advantage of providing an additional monitoring modality, namely monitoring the rate of increase or decrease of systolic blood pressure. An additional alarm may be activated when the systolic blood pressure is seen to experience a rapid rate of decrease—even before the actual value has reached an allowed safe threshold.

Importantly, throughout the entire ischemic duration interval, the pressure in either bladder may not be allowed by the controller 250 to drop below the most recent known value of the limb occlusion pressure so as not to compromise the efficacy of ischemic preconditioning treatment.

During the limb reperfusion duration, a similar but "reversed" blood pressure measurement procedure may be conducted by the controller 250 on a periodic basis to detect the diastolic blood pressure of the subject. In one embodiment of the invention, during at least a portion of the reperfusion duration both bladders are inflated by the controller 250 to a level about the previously detected or estimated diastolic blood pressure of the subject. The new diastolic blood pressure is detected when the distal or proximal bladder has pulsations amplitude equal to that measured previously for diastolic pressure. In another embodiment, the diastolic pressure is indicated by a proximal cuff pressure value associated with a rapid drop in pulsation amplitude of the distal bladder.

In its most comprehensive form, the method of the present invention allows for continuous monitoring of the blood pressure of the subject throughout the entire ischemic preconditioning treatment protocol without compromising its efficacy and without requiring the use of another limb for monitoring purposes. Systolic blood pressure in this case is measured by the controller using one of the above described methods during the ischemic duration interval followed by an optional calculation of estimated diastolic blood pressure. During reperfusion duration, the diastolic blood pressure is measured as well on a near-continuous or periodic basis, followed by an optional calculation of an estimated systolic blood pressure of the subject. One or both systolic and diastolic blood pressure values are presented on a display of the device.

For patients with a weak pulse, an additional improvement contemplated to be within the scope of the present invention may be an artificial pulse generator located at the proximal portion or above the proximal bladder of the device. Such pulse generator may be a narrow rapidly-inflatable third bladder or a mechanical artery-compression means. Activation of this pulse generator causes a series of artery compressions. Depending on the degree of limb compression by the proximal bladder, these pulsations may or may not reach the distal bladder. The proximal bladder pressure at which these pulsations no longer reach the distal bladder is designated as a systolic pressure of the subject. To further improve the accuracy of pressure detection, the intervals between the pulsations of the artificial pulse generator may be uneven so that the device can easily discern between the natural and artificial pulse.

The above described methods for detecting blood pressure are conducted during gradual deflation of the proximal bladder 212. To conduct the pressure measurement on inflation of this bladder, another method of the present invention includes the steps of inflating the distal bladder to at least a pressure point when its pressure pulsatility may be reliably detected. The proximal bladder 212 may then be inflated to that same pressure and then continued to be inflated (optionally with a slower rate of inflation) until a rapid decrease in pressure pulsatility is detected in the distal bladder 213 indicating that the pressure in the proximal bladder has reached a systolic pressure. The pressure in the distal bladder 213 may then be increased to match that of the proximal bladder 212. Inflation of both bladders may be done at the same time according to another method of the invention.

A simplified version of the device is provided in yet another embodiment of the invention in which the controller may include two or only one pressure sensor, which may be connected at first or permanently to monitor pressure in the distal bladder. The controller is programmed for delivery of ischemic preconditioning treatment protocol as described above. The novel feature in this embodiment is the method of cuff inflation including inflating both bladders to a first pressure sufficient to detect pressure pulsations in the distal bladder and then to a second pressure to detect a rapid decrease in the amplitude of such pulsation.

The controller in this embodiment may be programmed to first cause inflation of the distal bladder to a first pressure at which pressure pulsations are clearly detected in the distal bladder. The proximal bladder may be inflated to the same first pressure in parallel with the inflation of the distal bladder or after the distal bladder is already inflated to the first pressure. Once the pressure pulsations are identified in the distal bladder, the bladders are inflated (in parallel or starting with a proximal bladder first) to a second pressure when the amplitude of pressure pulsations in the distal bladder rapidly decreases, whereby defining systolic pressure of the subject. Optionally, inflation from the first pressure to the second pressure may be done at a slower inflation rate. This second pressure is sufficient to maintain limb occlusion throughout the ischemic duration interval. During cuff deflation, both bladders are deflated to or below the first pressure to allow for limb reperfusion. To separate pressure signals of one bladder from another in order not to contaminate the pressure signal of the distal bladder with the noise from the proximal bladder, a calibrated air flow restrictor may be positioned in an air line between the bladders. In another embodiment, a valve separating one bladder from another is installed. It may be operated by the controller to intermittently isolate and then reconnect two bladders so that pressure monitoring in the distal bladder can be done during periods of separation of the bladders. Reconnecting bladders together allows equalizing pressure in both bladders.

One advantage of this embodiment is that the level of cuff inflation (the second pressure) is defined at the beginning of each cuff inflation interval and therefore may track the changes in subject's blood pressure.

After the completion of the ischemic preconditioning treatment protocol, the device of the invention may be configured to resume the blood pressure monitoring mode as described above and to initiate a 1- or 2-hour countdown indicating the time available for reperfusion without a loss of the preconditioning effect. This mode may be particularly useful after completion of percutaneous intervention while the subject is transferred from the catheterization laboratory to the step-down unit.

Ischemic Preconditioning Devices for Use in a Percutaneous Intervention Setting

Release of emboli during a percutaneous intervention can cause harmful effect downstream of the point of such release. It is known for example that elective percutaneous coronary intervention (PCI) procedures sometimes cause significant elevation in the level of Troponin and other infarct-indicating enzymes. This is believed to be a result of release of microembolic particles at the site of stenosis and stent implantation, these particles causing a number of obstructions in smaller arteries downstream. Carotid percutaneous interventions are known to sometimes exhibit a similar effect on the brain tissue.

In view of this risk, all percutaneous procedures may benefit from remote ischemic preconditioning treatment. Recent studies with manually-delivered ischemic preconditioning using a simple blood pressure cuff have confirmed such benefit for elective PCI patients as measured by reduction in Troponin release at 24 hrs after the procedure. As maximum benefit is derived when ischemic preconditioning is completed just prior to such percutaneous intervention, provided herein are descriptions of the novel device of the invention adapted to be used in the catheterization laboratory environment.

Inserting a catheter percutaneously requires making an opening in an artery, typically in a femoral artery. After the percutaneous intervention procedure is finished, this arterial opening has to be reliably closed to avoid postprocedural bleeding. Various invasive and non-invasive devices are available on the market to accomplish this purpose. The recent trend in vascular sealing is to avoid highly invasive closure device acting on the arterial site itself. Non-invasive or minimally invasive devices providing overall compression of the insertion site are gaining in popularity due to their simplicity and ease of use.

The novel device of the present invention is a combination device for ischemic preconditioning and vascular sealing. It may be first applied to deliver a series of limb occlusions for the purposes of ischemic preconditioning and then reapplied again after the completion of percutaneous intervention to cause extended tissue compression for the purposes of external vascular sealing. The device may be configured to be used on either an arm or a leg of a subject. In one embodiment of the invention, the device is adapted for femoral puncture site closure.

According to another embodiment (not shown on the drawings), the device of the invention includes a single occlusion bulb designed and sized to occlude the target artery such as a femoral artery. It can be retained over the arteriotomy by a retaining means such as an adhesive sheet, a belt, attached to a cuff wrapped about the thigh, or a surrounding clamp wrapped about the patient. Once the bulb is positioned over the future arteriotomy site before the procedure, it may be periodically inflated and deflated by a controller to cause ischemic preconditioning occlusions of the leg according to a predetermined ischemic preconditioning treatment protocol. Such treatment protocol may include a predetermined number of ischemic duration and reperfusion intervals similar to what is described above. Optional monitoring of distal perfusion or distal oxygenation may be used to ensure full arterial occlusion, for example a pedal Doppler or a pulse-oxymeter. Upon completion of the ischemic preconditioning procedure, the bulb may be lifted or entirely moved out of the way to allow for femoral access and catheter insertion. The device includes provisions to easily return the bulb to the same original position later after the percutaneous procedure is finished. One practical way to achieve this may be to leave in place the main retaining means of the bulb on the patient's limb (adhesive tabs or a retaining belt) and provide additional detaching means to move only the bulb itself from its original position and to store it off the arteriotomy site. When the catheterization procedure is finished and the catheter is removed from the artery, the bulb may be returned to its original position. Optionally, the bulb may be equipped with a removable cover. Taking the cover off allows exposing a new sterile surface towards the wound after returning the bulb to the arteriotomy site. Reinflation of the bulb provides for tissue compression causing hemostasis and vascular sealing. In another embodiment of the device, after initial firm compression of the arteriotomy for a predetermined period of time such as 5 to 10 min or so, the controller may be configured to partially deflate the bulb. This will allow at least some blood flow past the arteriotomy. Thereafter the bulb may be gradually or periodically deflated again by the controller in predetermined increments of volume or pressure reduction so as to gradually decrease the tissue compression above the arteriotomy mimicking the manual hemostasis procedure.

A further configuration of the device 300 (see FIGS. 7-10) involves two inflatable bulbs or bladders—a first bladder 321 incorporated into a preconditioning cuff 320 and the second bladder 312 included in a vascular sealing subassembly 310. In one embodiment, this configuration includes a preconditioning cuff 320 sized according to the standard thigh cuff sizes described above. In another embodiment, the cuff 320 is sized to cover as much of the thigh length as possible so as to reduce subject's pain and discomfort. It also may further include a proximal bladder and a distal bladder as described above configured for blood pressure monitoring in addition to ischemic preconditioning. Cuff closure means (not shown), for example Velcro are provided to ensure a snug adjustable fit over the subject's limb. When the cuff 320 may be wrapped around the thigh of the subject and the bladder 321 is inflated to a sufficient pressure (at least a limb occlusion pressure) by the controller 330 (which can be configured using any of the above described concepts), blood circulation to the thigh is interrupted. Attached to the preconditioning cuff 320 via an adjustable-position attachment means 340 (described below in more detail) is an inflatable vascular sealing assembly 310 with a second bladder 812. This bladder may be sized and pressurized to provide for full occlusive pressure over the femoral artery or only for maintaining hemostasis which is first achieved using a manual compression or another device-assisted technique. The controller 330 may be designed as a disposable or reusable part. It may be connected to both the preconditioning bladder 321 and the vascular sealing bladder 312 via independent attachment channels such as a dual channel tube 350 and/or internal air passages formed within other elements of the device (not shown).

The controller 330 may be configured to provide dual functionality of delivering ischemic preconditioning as described above and the vascular sealing capability to properly inflate, monitor, adjust if needed and gradually deflate the vascular sealing bladder 312. One advantageous novel method of operating the vascular sealing bladder 312 is to initially fully inflate it to sufficient pressure to cause full compression of the artery in order to establish initial hemostasis. The controller 330 may be configured to then deflate the bladder 312 at predetermined intervals of time or using predetermined gradually decreasing pressure levels. Another method of operating the bladder 312 is to use the preconditioning bladder 321 located on the thigh of the subject as a pressure sensor.

Above described methods of monitoring systolic and diastolic blood pressure values may be used in this configuration to allow detection of blood flow past the vascular sealing bladder 312. Flow detection methods may include operating both bladders as described above for the dual-bladder device, in which case the preconditioning bladder 321 may be inflated partially and treated as a distal bladder 213. In that case, following the initial full inflation of the vascular sealing bladder 312, complete occlusion of flow will be initially confirmed and then continuously indicated by the lack of pulsations or Korotkoff sounds as detected by monitoring pressure patterns in the preconditioning bladder 321. After a specified period of time, for example 5 to 10 minutes, a gradual deflation of the vascular sealing bladder 312 may be initiated by the controller 330 until a rapid increase of pulsation amplitude (or the presence of Korotkoff sounds) is detected in the preconditioning bladder 321 indicating restoration of at least a partial flow in the femoral artery. The next step may be deflating the vascular sealing bladder 312 until reduction in pulsation amplitude or cessation of Korotkoff sounds indicating restoration of full flow in the limb artery. At this point, the tissue around the artery is still compressed allowing for maintaining hemostasis. Thereafter, the vascular sealing bladder 312 may be further deflated and eventually removed from the patient. Additional intermittent points in deflation of the vascular sealing bladder 312 are also envisioned to further delay reduction of compressive force on the site of arteriotomy. At the end of the above described gradual or incremental deflation process, an optional alarm may be turned on by the controller 330 to attract the attention of a medical practitioner to the fact that the vascular sealing is complete. Adjustable user-selected programs or intervals of periodic deflation may be incorporated into the controller 330 so as to accommodate various clinical situations such as an obese person, or various levels of anticoagulation in the blood stream of the subject. These situations may be handled by switching from one predetermined deflation program to another. Manually set deflation intervals are further envisioned to provide the medical practitioner with needed discretion in using the device of the invention.

Adjustable-position attachment means 340 between the vascular sealing subassembly 310 and the ischemic preconditioning cuff 320 are now described in more detail. Attachment means 340 have to satisfy the following main functional requirement: allow for storage of the vascular sealing bladder 312 near or over the ischemic preconditioning cuff 320 in the least obtrusive way so as to minimize its protrusion above or to the side of the preconditioning cuff 320 during the ischemic preconditioning procedure. At the same time, after the completion of percutaneous catheterization procedure, the attachment means 340 should allow extension of the sealing subassembly 310 to the arteriotomy site and sufficient support of the vascular sealing bladder 312 when inflated so as to compress tissue over arteriotomy to achieve hemostasis. Importantly, this invention provides for a novel means of supporting the vascular sealing bladder 312 over the site of the arteriotomy, namely a using the preconditioning cuff 320 wrapped about the subject's thigh, the cuff 320 equipped with the vascular sealing bladder attachment means 340. This is different from other known devices which rely either on a skin adhesive or on a surrounding clamp wrapped about the subject's body.

Figure 9A:
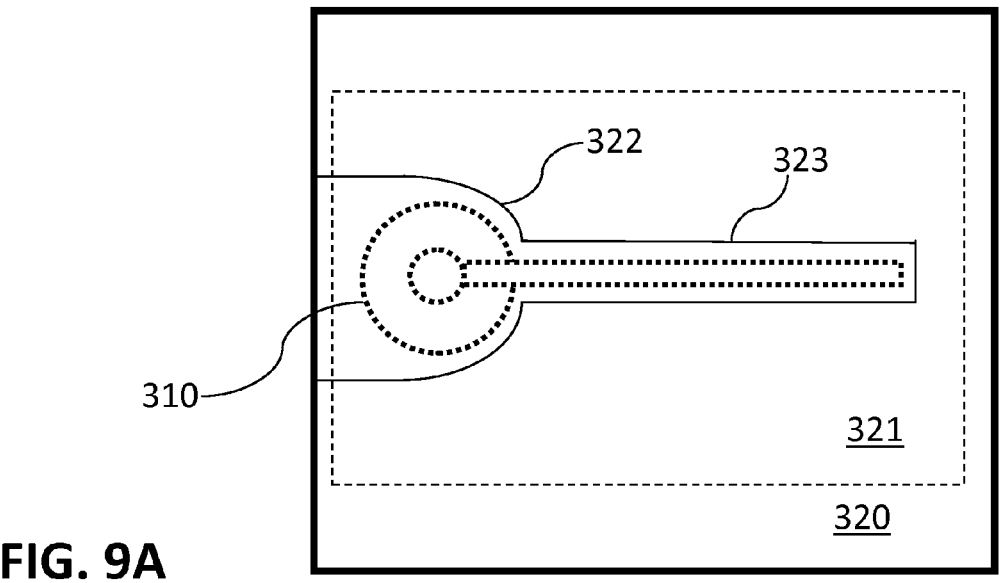
FIGS. 9A and 9B are collapsed and extended schematic illustrations of one specific embodiment of the device of the invention configured for performing both ischemic preconditioning and vascular sealing functions.
Figure 9B:
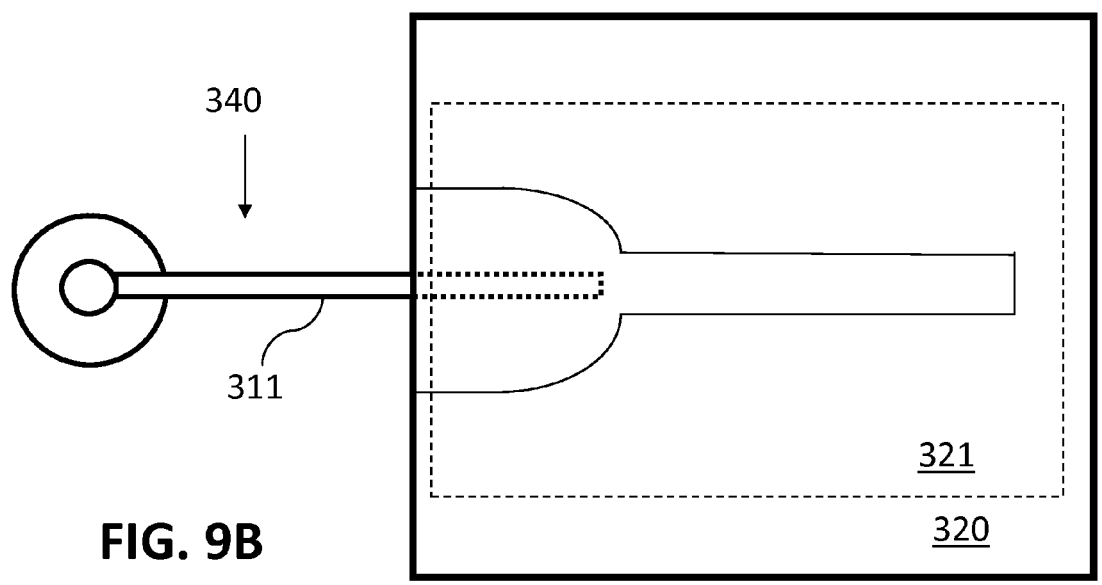

FIG. 9A shows a top view of one embodiment of the device of the invention presented in its collapsed configuration. The preconditioning cuff 320 includes a bladder 321 and a pocket comprising a wide section 322 sized to accept a vascular sealing subassembly 310. The pocket also contains a narrow long section 323 (optionally reinforced or made from a rigid material) sized to snuggly accept the attachment means 340. Attachment means 340 in turn comprises in one aspect of the invention a malleable member 311. Deployment of the sealing subassembly 310 may be achieved by partial extending it from the pocket 322 and bending the malleable member 311 so that the vascular sealing bladder 312 is positioned over the arteriotomy. Expanded configuration of the device is shown in FIG. 9B. Alternate configurations includes storing the vascular sealing subassembly 310 with the attachment means 340 separately and then attaching it to the preconditioning cuff 320, for example by inserting a member 311 into the pocket 323.

Figure 10:
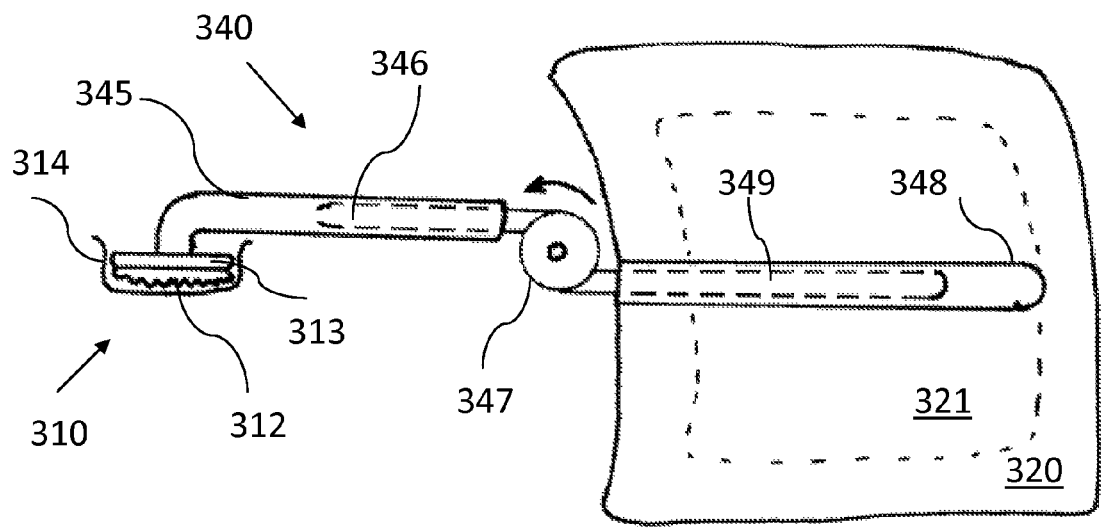
FIG. 10 is an illustration of another device adapted for the same purpose as that shown in FIGS. 9A and 9B.

FIG. 10 shows an expanded configuration of another embodiment of the device of the invention. Attachment means 340 allow for rotating the vascular sealing subassembly 310 from its storage position over the preconditioning cuff 320 to its operating position as shown in FIG. 10 using a rotating joint 347. Optionally, the joint 347 includes provisions (such as a ratcheting mechanism) allowing only one-way movement of the subassembly 310 in the direction of the arrow in FIG. 10. This precludes it from moving back towards it storage position. An optional release button may further be provided (not shown). Although rotation in a vertical plane is shown in FIG. 10, other orientations of the rotation plane for joint 347 are also envisioned including a horizontal and tilted orientation. Additionally, joint 347 allows for adjustment of the bulb position to the left or to the right from the cuff when viewed from above.

Attachment means 340 may additionally include provisions allowing extending the position of the bladder 312 lengthwise and away from the cuff 320. One or two sliding joints are provided for this purpose. FIG. 10 shows a first sliding joint comprising a tube 345 and a rod 346 and a second sliding joint comprising a tube 348 and a rod 349. These joints are designed to provide for sufficient range of length extension without compromising the strength of retaining the vascular sealing subassembly 310 by the cuff 320 over arteriotomy.

The sealing subassembly 310 comprises a vascular sealing bladder 312 attached to a disk 313 and optionally covered by a removable cover 314 to allow a sterile surface of the bladder 312 to be exposed towards the wound when the bladder 312 is placed over the arteriotomy site.

In another aspect of the invention, the attachment means may include one or two swivel joints and an extension member. The swivel joints may be made to include tightening clamps so as to retain their position. This embodiment provides an ability to reposition the vascular sealing subassembly from time to time by loosening and tightening clamps of the swivel joints. The presence of the swivel joints is also helpful in adjusting the angle between the occluding bladder and the skin so as to allow placing the bladder flat on the skin irrespective of the tissue curvature.

Figure 11:
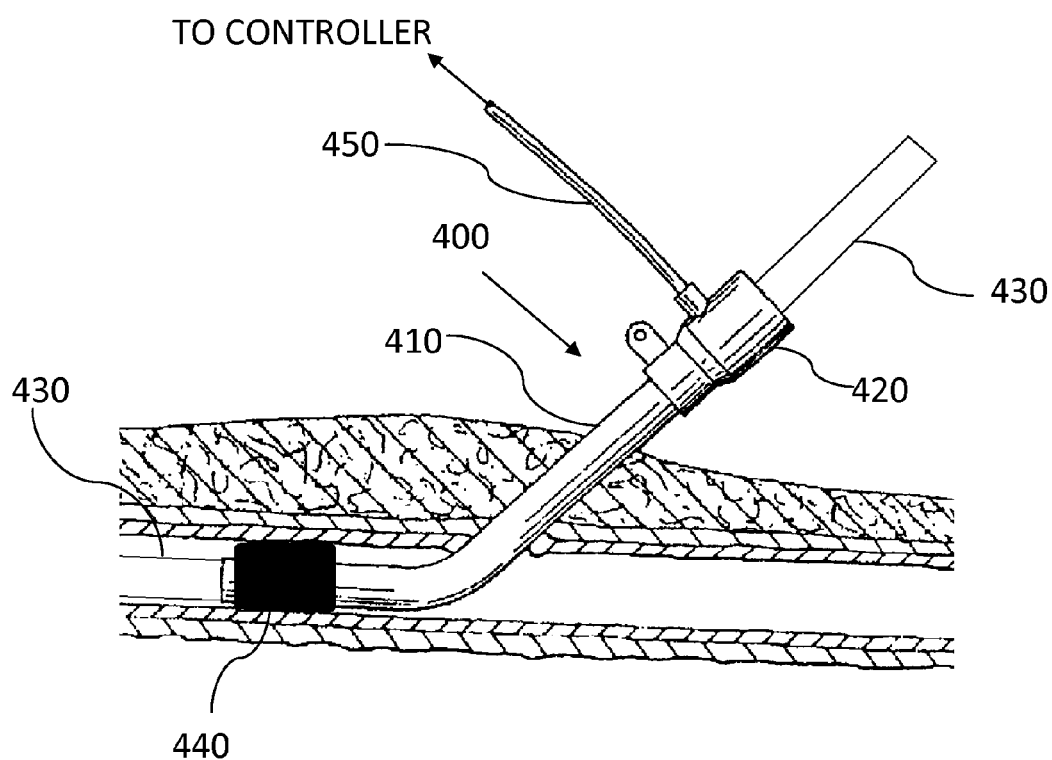
FIG. 11 is a side view of yet another device of the invention, namely an introducer sheath with a built-in balloon to provide an ischemic preconditioning functionality.

A Sheath Equipped for Ischemic Preconditioning for Use During a Catheterization Procedure FIG. 11 shows yet a further embodiment of the device of the invention adapted for use during a percutaneous intervention. It illustrates an introducer sheath configured for delivering of an ischemic preconditioning therapy prior, during, or after a catheterization procedure. The introducer sheath 400 of the invention comprises a sheath tube 410 extending from a hub 420. An inflatable occluding balloon 440 made for example from an elastic material such as silicone or latex may be located at the distal end of the sheath tube 410. Inflation of the balloon 440 can be accomplished by injecting air or liquid (such as saline) through a lumen 450, which may in turn be connected to an external controller (not shown). The balloon 440 may be sized to occlude the artery in which the sheath 400 is inserted. The balloon 440 may be further designed to have a low profile when deflated so as not to increase the thickness of the sheath tube 410. Other embodiments of the invention include means for mechanical expansion of a distal portion of a tube 410 which will accomplish the same result of occluding the artery. An intervention catheter 430 may be introduced through a sheath 400 using commonly known insertion techniques.

The controller may be configured to inflate and deflate the balloon 440 according to an ischemic preconditioning treatment protocol as described above, for example having 3-4 cycles of 3-5 min inflations and 3-5 min deflations. The controller may be designed as a reusable electronic device similar to that described above but sized to inject a smaller amount of air or liquid (saline) to inflate the balloon 440. In another embodiment, the controller may be made as a disposable attachment to the sheath 400 allowing for a semiautomatic operation of the device. The controller in that case may include one or more inflatable chambers that are pressurized all at the same time when filled by a syringe before the beginning of the percutaneous intervention procedure. An electrically- or mechanically-activated communication system may be provided to connect one chamber at a time to balloon 440 so as to cause inflation thereof. After a predetermined period of time, the balloon 440 may be vented to atmosphere or exposed to vacuum causing its deflation.

Additional useful provisions for the device of the invention include indicators of proper balloon inflation. Total occlusion of the artery may be monitored manually or with known devices to assess distal pulse. Lack of distal pulse indicates proper balloon inflation. An optional indicator window (not shown) may be incorporated in the hub 420 which in turn may be connected with an arterial opening close to the location of the balloon 440 but spaced a short distance towards the hub. Under arterial pressure, a pulsating blood meniscus may be visible through the window. Inflating the balloon 440 and occluding the artery may be confirmed by cessations of these pulsations. Deflation of balloon 440 may be verified by resuming pulsations of blood meniscus through the window.

In use, the sheath 400 may be inserted in the arterial system of the subject at the beginning of catheterization procedure which is then carried out as usual. During the intervention procedure, the side arm lumen 450 is attached to the controller and the balloon 440 may be operated to cause ischemic preconditioning in the patient's limb. After the catheterization procedure and ischemic preconditioning procedure are complete, the sheath may be withdrawn in a usual manner. This device of the invention allows for easy and seamless delivery of ischemic preconditioning during the percutaneous intervention procedure without the need to finish preconditioning before revascularization.

In another aspect of the invention, a dual-lumen introducer sheath of the invention is provided with a generally oval or egg-like cross-sectional shape. This cross-sectional shape will allow incorporating the balloon inflation lumen without compromising the circular main segment of the sheath and with minimizing the trauma to the artery. In another embodiment of the invention, the sheath is positioned in the artery with the long axis of the oval or egg-like cross-sectional shape oriented orthogonally to the longitudinal axis of the artery. This orientation will provide for the least disturbance to the media layer of the artery, containing arterial contraction muscles.

The concept of building an ischemic preconditioning element into an existing percutaneous device described above may be expanded beyond the introducer sheath to other catheters and delivery systems. One example of such system is a delivery device for a stent-graft device used during a percutaneous treatment or an aortic or abdominal aneurysm. As ischemic preconditioning treatment may be useful for patients undergoing these procedures. Incorporating a preconditioning expandable balloon within a stent delivery system at a projected location of femoral or iliac artery may facilitate delivering of preconditioning benefits to a broad group of patients.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

I claim:

1. A device for remote ischemic preconditioning, the device comprising:
    a cuff sized to retract about a limb of a subject,
    a controller connected to said cuff, said controller configured to inflate and deflate said cuff according to a remote ischemic preconditioning treatment protocol, said treatment protocol includes at least two sequentially performed treatment cycles, each of said treatment cycles comprising:
        inflating said cuff to a cuff pressure at or above a limb occlusion pressure of the subject,
        maintaining said cuff pressure at or above said limb occlusion pressure for a period of at least about one minute, and
        deflating said cuff for at least about one minute to restore blood flow in said limb, wherein during maintaining said cuff pressure at or above said limb occlusion pressure, said controller is further configured to vary said cuff pressure at least once after a predetermined period of time during at least one of said treatment cycles.

2. The device as in claim 1, wherein said controller is further configured to detect a systolic blood pressure of the subject during varying of said cuff pressure.

3. The device as in claim 2, wherein said controller is further configured to inflate said cuff pressure to a vicinity of a previously recorded systolic blood pressure during varying of said cuff pressure.

4. The device as in claim 3, wherein said controller is further configured to determine a diastolic pressure of the subject, whereby said subject is under continuous hemodynamic surveillance throughout said ischemic preconditioning treatment.

* * * * *